(12) United States Patent
Andersen et al.

(10) Patent No.: US 7,122,522 B2
(45) Date of Patent: Oct. 17, 2006

(54) ALPHA-FETOPROTEIN PEPTIDES AND USES THEREOF

(75) Inventors: Thomas T. Andersen, Albany, NY (US); James A. Bennett, Delmar, NY (US); Herbert I. Jacobson, Albany, NY (US); Fassil B. Mesfin, Albany, NY (US)

(73) Assignee: CLF Medical Technology Acceleration Program, Inc., Clifton Park, NY (US)

( * ) Notice: Subject to any disclaimer, the term of this patent is extended or adjusted under 35 U.S.C. 154(b) by 631 days.

(21) Appl. No.: 10/300,530

(22) Filed: Nov. 20, 2002

(65) Prior Publication Data

US 2006/0199769 A1 Sep. 7, 2006

Related U.S. Application Data

(60) Provisional application No. 60/409,109, filed on Sep. 9, 2002, provisional application No. 60/397,012, filed on Jul. 19, 2002, provisional application No. 60/397,373, filed on Jul. 19, 2002, provisional application No. 60/340,926, filed on Dec. 7, 2001, provisional application No. 60/331,841, filed on Nov. 20, 2001.

(51) Int. Cl.
*A61K 38/00* (2006.01)
(52) U.S. Cl. ......................................... 514/15; 530/328
(58) Field of Classification Search ........ 530/324–328, 530/317, 300, 350; 514/15
See application file for complete search history.

(56) References Cited

U.S. PATENT DOCUMENTS

| | | | | |
|---|---|---|---|---|
| 5,674,842 A | | 10/1997 | Mizejewski | 514/12 |
| 5,707,963 A | * | 1/1998 | Mizejewski | 514/12 |
| 6,306,832 B1 | | 10/2001 | Pietras | 514/44 |

OTHER PUBLICATIONS

Skolnick et al. (Trends in Biotech., 18(1):34-39, 2000).*
Allen, et al., "Purification of Alpha-Fetoprotein from Human Cord Serum with Demonstration of its Antiestrogenic Activity", *Biochimica et Biophysica Acta*, 1202:135-142 (1993).
Bedo, et al., "Retinoic Acid Regulates Growth Hormone Gene Expression", *Nature*, 339:231-234 (1989).
Bennett, et al., Abstract Only, "Transformation of Alpha-Fetoprotein (AFP) to a Negative Regulator of Estrogen-Dependent Growth by Ligands of the Steroid/Thyroid Hormone Receptor Superfamily", *Proceedings of the American Association for Cancer Research*, 34:244 (1993).
Bennett, et al., Abstract Only, "An α-Fetoprotein-Derived Peptide Inhibits Estrogen Receptor Positive Breast Cancers, Sensitive and Resistant to Tamoxifen", *Proc. Amer. Assoc. Can. Res.*, 42: 238 (2001).
Bennett, et al., "A Peptide Derived from α-Fetoprotein Prevents the Growth of Estrogen-Dependent Human Breast Cancers Sensitive and Resistant to Tamoxifen", *PNAS*, 99:2211-2215 (2002).
Collins, et al., "Spontaneous Cessation of Friend Murine Leukemia Virus Production by Leukemia Cell Line Y57: Overgrowth by Nonproducer Cells", *J. National Cancer Institute*, 64:11531159 (1980).
Conti, et al., "Thyroid Hormone Effect on α-Fetoprotein and Albumin Coordinate Expression by a Human Hepatoma Cell Line", *Biochimica et Biophysica Acta*, 1008:315-321 (1989).
Dauphinee, et al., Abstract Only, "Peptide Suppression of Breast Cancer Growth: In Search of Mechanisms by Identification of Cellular Targets", *Breast. Can. Res. Treat.*, 64:109 (2000).
Dietrich, "New Aspects of Steroid Hormone Dependent Tumor Growth", *Arch. Geschwulstforsch.*, 60:149-160 (1990).
Eisele, et al., "Studies on a Growth-Inhibitory Peptide Derived from Alpha-Fetoprotein and Some Analogs", *J. Pept. Res.*, 57:29-38 (2001).
Eisele, et al., "Studies on Analogs of a Peptide Derived from Alpha-Fetoprotein Having Antigrowth Properties", *J. Pept. Res.* 57:539-546 (2001).
Evans, "The Steroid and Thyroid Hormone Receptor Superfamily", *Science*, 240:889-895 (1988).
Garreau, et al., Phytoestrogens: New Ligands for Rat and Human α-Fetoprotein, *Biochimica et Biophysica Acta*, 1094:339-345 (1991).
Gekonge, et al., Abstract Only, "Regulation of Estrogen Activity by an Antiestrotrophic α-Fetoprotein Peptide", *Proc. Amer. Assoc. Can. Res.*, 42: 239 (2001).
Jacobson, et al., "Inhibition of Estrogen-Dependent Breast Cancer Growth by a Reaction Product of α-Fetoprotein and Estradiol", *Cancer Research*, 50:415-420 (1990).
Jacobson, et al., "Anti Breast -Cancer Peptides Derived from Alpha-Fetoprotein", Abstract published in Cancer Detection and Prevention 2000; 24 (Supplement 1);, http://www.cancerprev.org/Journal/Issues/24/101/409/3220 (2000).

(Continued)

*Primary Examiner*—Sheela J. Huff
(74) *Attorney, Agent, or Firm*—Ivor R. Elrifi; Naomi S. Biswas, Esq.; Mintz Levin

(57) ABSTRACT

Therapeutic compounds which are cell proliferation modulators, preferably inhibitors. These modulators contain amino acid structures that are arranged as a hydrophilic analog of an alpha-fetoprotein. The modulator may be a peptide itself, e.g., an octapeptide like that of SEQ ID NO: 5; a peptidomimetic; or may be in the form of a pharmaceutically acceptable scaffold, such as a polycyclic hydrocarbon to which is attached the necessary amino acid structures for biological and/or chemical activity. The modulators of the invention are distinguished in one aspect over previous compounds in that they are orally active, and therefore do not have to be injected into the patient. The compositions and methods are useful for reducing estrogen-stimulated growth of cells, and treating or preventing cancer, such as breast cancer. The treatment or prevention methods can include the use of tamoxifen therapy in combination with the peptide therapy.

10 Claims, 19 Drawing Sheets

OTHER PUBLICATIONS

Jacobson, et al., "Estradiol-Induced Changes in Spectral and Biological Properties of Alpha-Fetoprotein", *Tumor Biology*, 11:104 (1990).

Jacobson, et al., "Pregnancy-Altered Breast Cancer Risk: Mediated by Maternal Serum AFP?", in *Biological Activities of Alpha$_1$-Fetoprotein*, Chapter 8, vol. II, pp. 93-100.

Keel, et al., "Purified Human α-Fetoprotein Inhibits Follicle-Stimulating Hormone-Stimulated Estradiol Production by Porcine Granulosa Cells in Culture", *Molecular and Cellular Endocrinology*, 94:21-25 (1993).

Keel, et al., "Purified Human Alpha-Fetoprotein Inhibits Growth Factor-stimulated Estradiol Production by Porcine Granulosa Cells in Monolayer Culture", *Endocrinology*, 130:3715-3717 (1992).

Larner, et al., "Binding of Estradiol-17-Fatty Acid Esters to Plasma Proteins", *Endocrinology*, 121:738-744 (1987).

Li, et al., "AFP-L3: A New Generation of Tumor Marker for Hepatocellular Carcinoma", *Clinica Chimica Acta*, 313:15-19 (2001).

MacColl, et al., "Interrelationships Among Biological Activity, Disulfide Bonds, Secondary Structure, and Metal Ion Binding for a Chemically Synthesized 34-Amino-Acid Peptide Derived from α-Fetoprotein", *Biochimica et Biophysica Acta*, 1528: 127-134 (2001).

Mesfin, et al., "Alpha-Fetoprotein-Derived Antiestrotrophic Octapeptide", *Biochimica et Biophysica Acta*, 1501: 33-43 (2000).

Mesfin, et al., Abstract Only, "Anti-Estrotrophic and Anti-Breast Cancer Activity of an AFP-Derived Octapeptide", *Proc. Amer. Assoc. Can Res.*, 41: 375 (2000).

Mesfin, et al., Abstract Only, "Novel Analogs in an Anti-Breast Cancer Octapeptide", *Proc. Amer. Assoc. Can. Res.*, 42: 778-779 (2001).

Mesfin, et al., "Development of a Synthetic Cyclized Peptide Derived from α-Fetoprotein that Prevents the Growth of Human Breast Cancer", *J. Pept. Res.*, 58: 246-256 (2001).

Mizejewski, et al., "Alpha-Fetoprotein Derived Synthetic Peptides: Assay of an Estrogen-Modifying Regulatory Segment", *Molec. Cell. Endo.*, 118:15-23 (1996).

Mizejewski, et al., "Separation of the Estrogen-Activated Growth-Regulatory Forms of Alpha-Fetoprotein in Mouse Amniotic Fluid", *Biology of Reproduction*, 42:887-898 (1990).

Mizejewski, et al., "Alpha-Fetoprotein Can Regulate Growth in the Uterus of the Immature and Adult Ovariectomized Mouse", *J. Reprod. Fert.*, 85:177-185 (1989).

Mizejewski, et al., "Studies of the Intrinsic Antiuterotropic Activity of Murine Alpha-Fetoprotein", *Tumor Biology*, 7:19-36 (1986).

Mizejewski, et al., "Estradiol-Activated α-Fetoprotein Suppresses the Uterotropic Response to Estrogens", *Proc. Natl. Acad. Sci. USA*, 80:2733-2737 (1983).

Mizejewski, "An Apparent Dimerization Motif in the Third Domain of Alpha-Fetoprotein: Molecular Mimicry of the Steroid/Thyroid Nuclear Receptor Superfamily", *BioEssays*, 15:427-432 (1993).

Mizejewski, "New Insights into AFP Structure and Function: Potential Biomedical Applications", in *Alpha-Fetoprotein and Congenital Disorders*, G.J. Mizejewski and I.H. Porter, Eds., Academy Press, Inc., Orlando, Florida, pp. 5-34 (1985).

Mizejewski, et al., "Alpha-Fetoprotein in a Dual Regulator of Growth in Estrogen-Responsive Tissues", in *Biological Activities of Alpha$_1$-Fetoprotein*, G.J. Mizejewski and H.I. Jacobson, Eds., CRC Press, Inc., Boca Raton, Florida, vol. I, pp. 71-82 (1987).

Mizejewski, et al., "AFP Modification of Biologic Response in Estrogen-Sensitive Tissues: Use of *In Vitro* Models", in *Biological Activities of Alpha$_1$-Fetoprotein*, G.J. Mizejewski, B.R. Stanton, and H.I. Jacobson, Eds., CRC Press, Inc., Boca Raton, Florida, vol. II, pp. 59-74 (1989).

Nunez, et al., "The Physicochemical and Biological Properties of Alpha-Fetoprotein Depend on its Ligand Environment", *J. Nucl. Med. Sci.*, 33:18-26 (1989).

Rosebrock, et al., "Immunoprecipitation Assay of Alpha-Fetoprotein Synthesis by Cultured House Hepatoma Cells Treated with Estrogens and Glucocorticords", *Differentiation*, 19:168-178 (1981).

Savu, et al., "Mouse α$_1$-Fetoprotein and Albumin", *J. Biol. Chem.*, 256:9114-9418 (1981).

Sonnenschein, et al., "Growth Inhibition of Estrogen-Sensitive Tumor Cells in Newborn Rats. Probable Role of Alpha-Fetoprotein", *J. National Cancer Institute*, 63:835-841 (1979).

Sonnenschein, et al., "Age-Dependent Growth Inhibition of Estrogen-Sensitive Rat Mammary Tumors. Probable Role of Alpha-Fetoprotein", *J. National Cancer Institute*, 64:1141-1146 (1980).

Soto, at al., "Control of Growth of Estrogen-Sensitive Cells: Role for α-Fetoprotein", *Proc. Natl. Acad. Sci. USA*, 77:2084-2087 (1980).

Vakharia, et al., "Human Alpha-Fetoprotein Peptides Bind Estrogen Receptor and Estradiol, and Suppress Breast Cancer", *Breast. Can. Res. Treat*, .63:41-52 (2000).

Wahli, et al., "Superfamily of Steroid Nuclear Receptors: Positive and Negative Regulators of Gene Expression", *FASEB*, 5:2243-2249 (1991).

Wan, et al., "The Effects of Retinoic acid on the Expression of α-Fetoprotein and Albumin Genes in Rat Hepatoma Cell Lines", *Differentiation*, 50:107-111 1992).

International Search Report for PCT/US02/37070, mailed on Jul. 10, 2003.

\* cited by examiner

% INHIBITION OF E₂-STIMULATED GROWTH OF IMMATURE MOUSE UTERUS vs μg OF PEPTIDE EMTOVNOG SEQ ID NO: 4

Fig. 4A

```
                              SEQUENCE LISTING

<160> NUMBER OF SEQ ID NOS: 12

<210> SEQ ID NO 1
<211> LENGTH: 9
<212> TYPE: PRT
<213> ORGANISM: Homo sapiens
<220> FEATURE:
<221> NAME/KEY: MOD_RES
<222> LOCATION: (4)
<223> OTHER INFORMATION: 4Hyp
<220> FEATURE:
<221> NAME/KEY: MOD_RES
<222> LOCATION: (7)
<223> OTHER INFORMATION: 4Hyp

<400> SEQUENCE: 1

Glu Lys Thr Pro Val Asn Pro Gly Asn
  1               5

<210> SEQ ID NO 2
<211> LENGTH: 8
<212> TYPE: PRT
<213> ORGANISM: Homo sapiens

<400> SEQUENCE: 2

Gln Met Thr Pro Val Asn Pro Gly
  1               5

<210> SEQ ID NO 3
<211> LENGTH: 9
<212> TYPE: PRT
<213> ORGANISM: Homo sapiens

<400> SEQUENCE: 3

Gln Met Thr Pro Val Asn Pro Gly Glu
  1               5

<210> SEQ ID NO 4
<211> LENGTH: 8
<212> TYPE: PRT
<213> ORGANISM: Homo sapiens
<220> FEATURE:
<221> NAME/KEY: MOD_RES
<222> LOCATION: (4)
<223> OTHER INFORMATION: 4Hyp
<220> FEATURE:
<221> NAME/KEY: MOD_RES
<222> LOCATION: (7)
<223> OTHER INFORMATION: 4Hyp

<400> SEQUENCE: 4

Glu Met Thr Pro Val Asn Pro Gly
  1               5

<210> SEQ ID NO 5
<211> LENGTH: 9
<212> TYPE: PRT
<213> ORGANISM: Homo sapiens
```

```
<220> FEATURE:
<221> NAME/KEY: MOD_RES
<222> LOCATION: (4)
<223> OTHER INFORMATION: 4Hyp
<220> FEATURE:
<221> NAME/KEY: MOD_RES
<222> LOCATION: (7)
<223> OTHER INFORMATION: 4Hyp

<400> SEQUENCE: 5

Glu Met Thr Pro Val Asn Pro Gly Gln
  1               5

<210> SEQ ID NO 6
<211> LENGTH: 8
<212> TYPE: PRT
<213> ORGANISM: Homo sapiens

<400> SEQUENCE: 6

Glu Met Thr Pro Val Asn Pro Gly
  1               5

<210> SEQ ID NO 7
<211> LENGTH: 9
<212> TYPE: PRT
<213> ORGANISM: Homo sapiens

<400> SEQUENCE: 7

Glu Met Thr Pro Val Asn Pro Gly Gln
  1               5

<210> SEQ ID NO 8
<211> LENGTH: 9
<212> TYPE: PRT
<213> ORGANISM: Homo sapiens
<220> FEATURE:
<221> NAME/KEY: MOD_RES
<222> LOCATION: (4)
<223> OTHER INFORMATION: 4Hyp

<400> SEQUENCE: 8

Glu Met Thr Pro Val Asn Pro Gly Gln
  1               5

<210> SEQ ID NO 9
<211> LENGTH: 9
<212> TYPE: PRT
<213> ORGANISM: Homo sapiens
<220> FEATURE:
<221> NAME/KEY: MOD_RES
<222> LOCATION: (7)
<223> OTHER INFORMATION: 4Hyp

<400> SEQUENCE: 9

Glu Met Thr Pro Val Asn Pro Gly Gln
  1               5

<210> SEQ ID NO 10
<211> LENGTH: 8
<212> TYPE: PRT
<213> ORGANISM: human
<220> FEATURE:
<221> NAME/KEY: MOD_RES
<222> LOCATION: (7)
<223> OTHER INFORMATION: 4Hyp
```

-continued

```
<400> SEQUENCE: 10

Glu Met Thr Pro Val Asn Pro Gly
 1               5

<210> SEQ ID NO 11
<211> LENGTH: 8
<212> TYPE: PRT
<213> ORGANISM: Homo sapiens
<220> FEATURE:
<221> NAME/KEY: MOD_RES
<222> LOCATION: (4)
<223> OTHER INFORMATION: 4Hyp

<400> SEQUENCE: 11

Glu Met Thr Pro Val Asn Pro Gly
 1               5

<210> SEQ ID NO 12
<211> LENGTH: 9
<212> TYPE: PRT
<213> ORGANISM: Homo sapiens
<220> FEATURE:
<221> NAME/KEY: VARIANT
<222> LOCATION: (1)
<223> OTHER INFORMATION: Wherein "Xaa" is E or Q or N or an acetylated
      or acylated derivative thereof .
<220> FEATURE:
<221> NAME/KEY: VARIANT
<222> LOCATION: (2)
<223> OTHER INFORMATION: Wherein "Xaa" is M or K or an analogue thereof.
<220> FEATURE:
<221> NAME/KEY: VARIANT
<222> LOCATION: (3)
<223> OTHER INFORMATION: Wherein "Xaa" is T or S or an amino acid
      providing steric hinderance and hydrophilicity.
<220> FEATURE:
<221> NAME/KEY: MOD_RES
<222> LOCATION: (4)
<223> OTHER INFORMATION: 4Hyp
<220> FEATURE:
<221> NAME/KEY: VARIANT
<222> LOCATION: (5)
<223> OTHER INFORMATION: Wherein "Xaa" is V or I or L or T or a
      beta-branched amino acid or a hydrophobic amino
      acid structure.
<220> FEATURE:
<221> NAME/KEY: VARIANT
<222> LOCATION: (7)
<223> OTHER INFORMATION: Wherein "Xaa" is P or S.
<220> FEATURE:
<221> NAME/KEY: MOD_RES
<222> LOCATION: (7)
<223> OTHER INFORMATION: 4Hyp
<220> FEATURE:
<221> NAME/KEY: VARIANT
<222> LOCATION: (9)
<223> OTHER INFORMATION: Wherein "Xaa" is an amino acid structure that
      may be present or absent; when present it may be Q or N.

<400> SEQUENCE: 12

Xaa Xaa Xaa Pro Xaa Asn Xaa Gly Xaa
 1               5
```

ALPHA-FETOPROTEIN PEPTIDES AND USES THEREOF

RELATED APPLICATIONS

This application claims the benefit of priority under 35 U.S.C. 119(e) to copending U.S. Provisional Application Nos. 60/331,841, filed Nov. 20, 2001; 60/340,926, filed Dec. 7, 2001; 60/397,373, filed Jul. 19, 2002; 60/397,012, filed Jul. 19, 2002; 60/409,109, filed Sep. 9, 2002; the entire contents of which are incorporated herein by reference.

STATEMENT AS TO FEDERALLY SPONSORED RESEARCH

This invention was made with U.S. Government support under National Institutes of Health Grant No. CA 87434 and U.S. Army Grant Nos. DAMD 17-99-1-9054 and DAMD 17-99-1-9370. The government has certain rights in the invention.

FIELD OF THE INVENTION

The subject invention is directed generally to alpha-fetoprotein, and more particularly to peptides derived from alpha-fetoprotein and their use to treat and/or prevent cancers, including breast cancer.

BACKGROUND OF THE INVENTION

Every year in the U.S., 180,000 new cases of breast cancer are diagnosed and approximately 60% of these are estrogen-receptor-positive (ER+) (Martin et al. 1994). Moreover, every year there are a substantial number of breast cancer recurrences, and many of these are ER+. Tamoxifen has been the mainstay for medical treatment of ER+ breast cancer and has provided significant clinical benefit (Fisher et al. 1989; Fisher et al. 1998). However, there are a substantial number of ER+ breast cancers that are refractory to tamoxifen due to either intrinsic or acquired resistance. New treatments for these ER+, tamoxifen-refractory breast cancers are needed, and some promising agents are currently being evaluated in clinical trial. Letrozole, which blocks estrogen synthesis by inhibiting aromatase; and goserelin, which stifles ovarian release of estrogen by inhibiting gonadotropin release; are both being tested for this purpose (Goss et al. 2001; Nystedt et al. 2000).

Several population and epidemiologic studies as well as laboratory studies have indicated that alpha-fetoprotein (AFP) interferes with estrogen-dependent responses, including the growth-promoting effects of estrogen on breast cancer (Bennett et al. 1998). For example, Couinaud et al. (1973) have reported that women with AFP-secreting hepatomas develop amenorrhea which self-corrects following removal of the hepatoma, and Mizejewski et al. (1983) have shown that AFP inhibits the responsiveness of the uterus to estrogen. Jacobson et al. (1989) and Richardson et al. (1998) have shown that elevated levels of AFP during pregnancy are associated with subsequent reduction in lifetime risk for breast cancer, and Jacobson et al. have hypothesized that this could be caused by a diminution in estrogen-dependent breast cancers (Jacobson et al. 1989). Sonnenschein et al. (1980) have shown in rats that an AFP-secreting hepatoma prevents the growth of an estrogen-dependent breast cancer in the same rat. Finally, it has been shown that AFP purified from a human hepatoma culture and then injected into tumor-bearing immune-deficient mice stopped the growth of ER+, but not estrogen-receptor-negative (ER−) human breast cancer xenografts in these mice, and did so by a mechanism different from that of tamoxifen (Bennett et al. 1998).

More recently, the active site of AFP responsible for its antiestrotrophic activity has been identified (Mesfin et al. 2000). It consists of amino acids 472–479 (SEQ ID NO: 6, EMTPVNPG), an 8-mer sequence in the 580-amino acid AFP molecule.

Aggregation of proteins and peptides has been seen with full length AFP as well as with subunits of AFP. Wu et al. (1985) showed that AFP tends to form aggregates, which may contribute to its loss of anti-estrotrophic activity during storage. Eisele et al. (2001) reported that oligomers of various sizes formed during storage of a 34-mer peptide (amino acids 447–480) derived from AFP. Similar aggregation behavior has been seen with a number of other protein and peptide pharmaceuticals, including human interferon-γ (Kendrick et al. 1998), human calcitonin (Bauer et al. 1994), insulin (Sluzky et al. 1991), and synthetic β-amyloid peptide (Hilbich et al. 1991; Christmanson et al. 1993; Halverson et al. 1990). Hughes et al. (1996) and Hilbich et al. (1992) reported inhibition of amyloid peptide aggregation by substitution of hydrophobic phenylalanine with hydrophilic threonine or by adding polylysine at the carboxy-terminus of the amyloid peptide.

SUMMARY OF THE INVENTION

Tamoxifen is currently the most widely used agent for the treatment of estrogen-responsive breast cancers and has provided significant benefit to women with this disease (Fisher et al. 1989; Fisher et al. 1998). However, one problem connected with its clinical use is that not all ER+ breast cancers are sensitive to tamoxifen. About one-third to one-sixth of the ER+ newly diagnosed breast cancers, depending on the lab cutoff for ER positivity, do not respond to tamoxifen (Jensen et al. 1996). Moreover, it is not uncommon that women whose disease is being successfully managed by tamoxifen therapy will in time experience recurrence during treatment apparently because their tumor has acquired resistance to the drug.

The invention provides novel compositions, pharmaceutical compositions, and methods of treatment of diseases involving cell proliferation, such as cancer, particularly breast cancer. These compositions provide advantages over tamoxifen therapy, and more options to the health practitioner in that adjunct therapies including the compositions of the invention and tamoxifen may also be used. The inventors have previously detailed the use of alpha-fetoproteins for treating and/or preventing cancers in U.S. Pat. No. 6,818,741, the content of which is incorporated herein by reference in its entirety.

The invention includes methods of treating or preventing breast cancer, comprising administering to a subject in need thereof an agent that blocks or inhibits ER phosphorylation, such that breast cancer is treated or prevented. The action of the agent may: block or inhibit the activation of the nuclear estrogen receptor (ER) by estradiol ($E_2$); or block or inhibit ER transcriptional activity; block or inhibit ER phosphorylation, e.g., at serine-118 of ER; by mitogen-activated protein kinase (MAPK).

The agents that may be used include the peptides comprising a hydrophilic analog of an alpha-fetoprotein, having the structure $Xaa_1$-$Xaa_2$-$Xaa_3$-O-$Xaa_4$-N-$Xaa_5$-G-$Xaa_6$ (SEQ ID NO: 12), wherein $Xaa_1$ is selected from the group consisting of E, Q, and N, or an acetylated or acylated derivative thereof;

$Xaa_2$ is selected from the group consisting of M and K, or analogs thereof, such as methionine sulfone, D-lysine, or acetylated L-lysine;

$Xaa_3$ is a structure providing steric hindrance and hydrophilicity and can be selected from the group consisting of T and S;

$Xaa_4$ is selected from the group consisting of V, I, L, T, a beta-branched amino acid structure, and a hydrophobic amino acid structure;

$Xaa_5$ is selected from the group consisting of P, O and S; and $Xaa_6$ is an amino acid structure which may be present or absent; when present, it may be used for cyclization and desirably may be selected from the group consisting of Q and N, or a substitution variant, peptidomimetic, retro-inverso isomer, or salt thereof.

The agent may also include one of the following: EKTOVNOGN (SEQ ID NO: 1) QMTPVNPG (SEQ ID NO:2); QMTPVNPGE (SEQ ID NO:3); EMTOVNOG (SEQ ID NO:4); EMTOVNOGQ (SEQ ID NO:5); EMTPVNPG (SEQ ID NO:6); EMTPVNPGQ (SEQ ID NO:7); EMTOVNPGQ (SEQ ID NO:8); and EMTPVNOGQ (SEQ ID NO:9.) or substitution variant, peptidomimetic, retro-inverso isomer, or salt thereof. The peptides may be linear or cyclic.

In another aspect the invention included methods of modulating an interaction between MAPK and ER, comprising adding, to a system containing MAPK and ER, an agent that modulates ER phosphorylation by mitogen-activated protein kinase (MAPK), such that an interaction between MAPK and ER is modulated. In a related aspect the invention includes methods of modulating $E_2$ activation of ER, comprising adding, to a system containing MAPK and ER, an agent that modulates ER phosphorylation by MAPK, such that $E_2$ activation of ER is modulated.

Breast cancer modulators may be identified using a method of the invention which comprises introducing into a system containing MAPK and ER with a putative agent that modulates ER phosphorylation by mitogen-activated protein kinase (MAPK); and determining the ability of the putative modulator to modulate ER phosphorylation in the test sample.

The invention also relates to assays for modulators of MAPK activation of ER (and to the modulators and use thereof in, e.g., treating cancer), wherein MAPK and ER are brought into contact with a putative modulator compound under conditions where ER activation, in the absence of modulator, is capable of occurring; and the degree of modulation of MAPK activation of ER caused by said modulator compound is measured.

In another aspect of the invention, cell-proliferating masses, e.g., breast cancer, may be detected noninvasively in a subject by administering to a subject a light-generating fusion protein (or a cell expressing the light-generating fusion protein), where the light-generating fusion protein includes a ligand binding site; and a targeting moiety which is one of the peptides of the invention; allowing for co-localization of light-generating fusion protein or cell and an entity; and imaging the localized light-generating fusion protein, thereby detecting a cell-proliferating disorder in the subject. The light-generating polypeptide moiety may be a bioluminescent or fluorescent polypeptide moiety, e.g., ferredoxin IV, green fluorescent protein, red fluorescent protein, yellow fluorescent protein, blue fluorescent protein, the luciferase family or the aequorin family.

The fusion proteins noted above are also part of the invention. Desirably the light-generating polypeptide moiety is responsive to phosphorylation changes at or near the cancer site. Fusion proteins may include a breast cancer targeting moiety; and a suicide payload.

A fusion protein comprising a targeting moiety which is one of the peptides of the invention, a suicide protein polypeptide moiety, and a light-generating polypeptide moiety which is responsive to phosphorylation changes at or near said breast cancer site, and methods of killing tumor cells using these proteins, are included in the invention.

Method of monitoring the cell-proliferating disorder treatment are part of the invention also, and involve administering to a subject an effective amount of a light-generating fusion protein of the invention, such that the cell-proliferating disorder is treated, and monitoring the ability of the fusion protein to inhibit cell proliferation by measuring the light generated by the fusion protein.

The invention provides therapeutic compounds that are cell proliferation modulators, preferably inhibitors. These modulators contain amino acid structures that are arranged as a hydrophilic analog of an alpha-fetoprotein. The modulator may be a peptide itself, e.g., an octapeptide like that of SEQ ID NO: 5; a peptidomimetic; or may be in the form of a pharmaceutically acceptable scaffold, such as a polycyclic hydrocarbon to which is attached the necessary amino acid structures for biological and/or chemical activity. The modulators of the invention are distinguished in one aspect over previous compounds in that they are orally active, and therefore do not have to be injected into the patient.

In one embodiment, the compounds are cell-proliferation modulators including the structure $Xaa_1$-$Xaa_2$-$Xaa_3$-O-$Xaa_4$-N-$Xaa_5$-G-$Xaa_6$ (SEQ ID NO: 12) wherein $Xaa_1$ may be E or Q or N or an acetylated or acylated derivative thereof; $Xaa_2$ may be M, K, or analogs thereof, such as methionine sulfone, D-lysine, or acetylated L-lysine; a biologically active peptide with resistance to proteolysis can be obtained by substituting $Xaa_2$ with acetylated L-lysine, D-lysine, D-ornithine, or L-ornithine; $Xaa_3$ is an amino acid structure providing steric hindrance and hydrophilicity and can be selected from the group consisting of T and S; $Xaa_4$ may be V, I, L, T, a beta-branched amino acid structure, or a hydrophobic amino acid structure; $Xaa_5$ may be P, O or S; and $Xaa_6$ is an amino acid structure which may be present or absent; when present, it may be used for cyclization and desirably may be selected from the group consisting of Q and N, or a salt, retro-inverso isomer, or peptidomimetic thereof. In certain embodiments, $Xaa_1$ is E; $Xaa_3$ is T; $Xaa_4$ is V; or $Xaa_5$ is O. In one preferred embodiment, the peptides comprise the sequence EMTOVNOGQ (SEQ ID NO: 5) or EKTOVNOGN (SEQ ID NO: 1). The peptides may be linear or cyclic.

The invention further relates to therapeutic compounds which are cell proliferation modulators, containing a pharmaceutically acceptable scaffold (such as a polycyclic hydrocarbon) to which is attached amino acid structures arranged as a hydrophilic analog of analpha-fetoprotein. One such therapeutic compound includes a scaffold to which is attached a structure of at least eight amino acid structures, a hydroxyproline amino acid structure, an asparagine amino acid structure, and a glycine amino acid structure, wherein the amino acid structures are arranged as a hydrophilic analog of an alpha-fetoprotein, and therapeutic compound modulates cell proliferation. Embodiments of these compounds are orally active, in distinction to predecessor compounds that required injection. The arrangement of the amino acid structure in the scaffold is desirably EMTOVNOGQ (SEQ ID NO: 5) or EKTOVNOGN (SEQ ID NO: 1) in the cyclic or linear forms.

In another embodiment, the arrangement of amino acid structures on the scaffold is as follows: a glutamic acid (E) or glutamine (Q) amino acid structure in the first position; a methionine (M) or lysine (K) amino acid structure, or analog thereof in the second position; a threonine (T) amino acid structure in the third position; a hydroxyproline (O) amino acid structure in the fourth position; a valine (V), isoleucine (I), or a beta-branched amino acid structure in the fifth position; an asparagine (N) amino acid structure in the sixth position; a hydroxyproline (O) amino acid structure in the seventh position; and a glycine (G) amino acid structure in the eighth position.

The invention further relates to peptides that are hydrophilic analogs of an alpha-fetoprotein, e.g., having the amino acid sequence EMTOVNOGQ (SEQ ID NO: 5) or EKTOVNOGN (SEQ ID NO: 1), or a substitution variant, peptidomimetic, retro-inverso isomer, or salt thereof. In one embodiment, the glutamic acid (E) may be replaced with glutamine (Q). In another embodiment, the amino group on the glutamic acid (E) is acetylated or acylated. In yet another embodiment, the methionine (M) may be replaced with lysine (K) or an analog thereof. The side chain of the hydroxyproline (O) adjacent to the T and V structures may be modified. The valine (V) may replaced by a beta-branched amino acid structure or hydrophobic amino acid structure, e.g., isoleucine (I); and/or the hydroxyproline (O) adjacent to the N and G structures may be replaced by serine (S).

The peptides may be provided as dimers or other multimers. Compositions comprising the peptide, an antibody that specifically binds to the peptide, methods of reducing estrogen-stimulated growth of cells using the peptides, as well as a method of treating or preventing cancer, such as breast cancer, are also provided. The treatment or prevention method can also desirably include the use of tamoxifen therapy in combination with the peptide therapy.

BRIEF DESCRIPTION OF THE DRAWING

These and other features and advantages of the invention will be evident from the following detailed description of preferred embodiments when read in conjunction with the accompanying drawings in which:

FIG. 1a shows the peptide dose-response. FIG. 1a shows the anti-estrotrophic activity as a function of peptide storage time at −20° C. in the lyophilized state, 1 µg peptide per mouse;

FIG. 3a shows the dose-response. FIG. 3b shows the effect of time in storage;

FIGS. 4a and 4b illustrate the anti-uterotrophic activity of peptide with hydroxyproline substituted for proline. FIG. 4a shows the dose response. FIG. 4b shows the effect of time in storage;

FIG. 6a shows the dose response. FIG. 6b shows the effect of time in storage;

FIG. 9a shows MCF-7 tumors. At day 30 after tumor implantation, tumor volumes in the $E_2$+Pep group and in the $E_2$+Tam group were significantly different from tumor volumes in the $E_2$ alone group, p<0.05, Wilcoxon Ranks Sum Test. FIG. 9b shows a MCF-7 subline made resistant to tamoxifen in culture. At day 30 after tumor implantation, tumor volumes in the $E_2$+Pep group but not in the $E_2$+Tam group were significantly different from tumor volumes in the $E_2$ alone group, p<0.05, Wilcoxon Ranks Sum Test;

DETAILED DESCRIPTION OF THE INVENTION

Figure 1A:
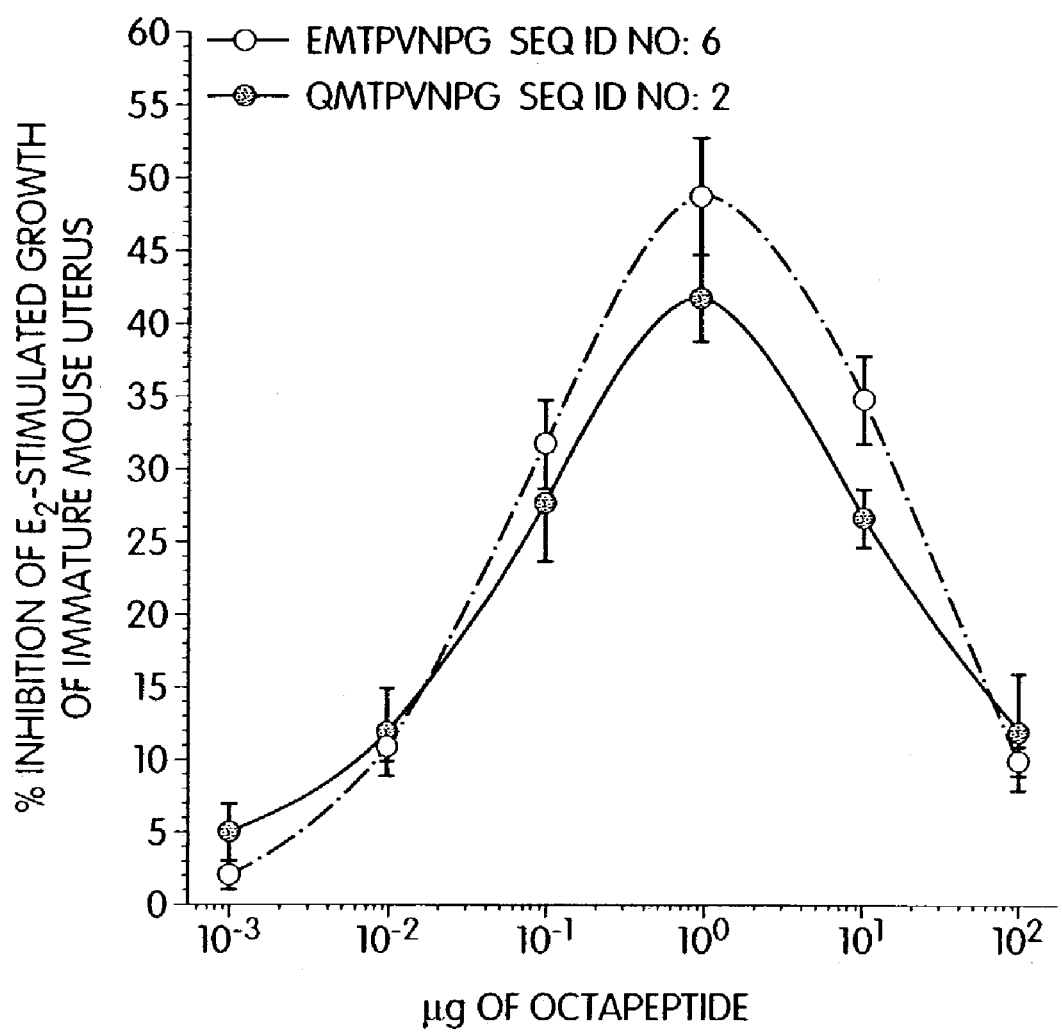
FIGS. 1a and 1b illustrate the anti-uterotrophic activity of octapeptide, SEQ ID NO: 2, QMTPVNPG, measured in the immature mouse uterine growth assay. Peptide or vehicle control was injected i.p. into immature female Swiss mice. One hour later 0.5 µg of $E_2$ vehicle control was injected i.p. into these mice. Twenty-two hours later, uteri were dissected and weighed. Percent inhibition of $E_2$-stimulated growth of uterus by peptide was calculated as described in Materials and Methods. There were five to eight replicate mice per treatment group.

As used herein, a "modulator" of cell proliferation is intended to refer to an agent that, when contacted with tissue or cells, alters cell proliferation. In the presence of a modulator of the invention, cell proliferation is "altered" or "modulated". The various forms of the term "alteration" or "modulation" are intended to encompass both inhibition of cell proliferation and promotion of cell proliferation. Cell proliferation is "inhibited" in the presence of the modulator when there is a decrease in the cell proliferation as compared to the amount and/or rate of cell proliferation in the absence of the modulator. The various forms of the term "inhibition" are intended to include both complete and partial inhibition of cell proliferation.

As used herein, "amino acid structure" (such as a "glycine structure", a "hydroxyproline structure" or a "asparagine structure") is intended to include the D-amino acid, as well as analogues, derivatives and mimetics of the amino acid that maintain the functional activity of the compound.

The structures of the modulators of the invention are further intended to include other peptide modifications, including analogues, derivatives and mimetics, that retain the ability of the modulator to alter cell proliferation as described herein. For example, a peptidic structure of a modulator of the invention may be further modified to increase its stability, bioavailability, solubility, etc. The terms "analogue", "derivative" and "mimetic" as used herein are intended to include molecules that mimic the chemical structure of a peptidic structure and retain the functional properties of the peptidic structure. Approaches to designing peptide analogs, derivatives and mimetics are known in the art. For example, see Farmer, P. S. in *Drug Design* (E. J. Ariens, ed.) Academic Press, New York, 1980, vol. 10, pp. 119–143; Ball, J. B. and Alewood, P. F. (1990) *J. Mol. Recognition* 3:55. Morgan, B. A. and Gainor, J. A. (1989) *Ann. Rep. Med. Chem.* 24:243; and Freidinger, R. M. (1989) *Trends Pharmacol. Sci.* 10:270. See also Sawyer, T. K. (1995) *Peptidomimetic Design and Chemical Approaches to Peptide Metabolism* in Taylor, M. D. and Amidon, G. L. (eds.) *Peptide-Based Drug Design: Controlling Transport and Metabolism*, Chapter 17; Smith, A. B. 3rd, et al. (1995) *J. Am. Chem. Soc.* 117:11113–11123; Smith, A. B. 3rd, et al. (1994) *J. Am. Chem. Soc.* 116:9947–9962; and Hirschman, R., et al. (1993) *J. Am. Chem. Soc.* 115:12550–12568.

As used herein, a "derivative" of a compound X (e.g., a peptide or amino acid) includes forms of X in which one or more reaction groups on the compound have been derivatized with a substituent group. Examples of peptide derivatives include peptides in which an amino acid side chain, the peptide backbone, or the amino- or carboxy-terminus has been derivatized (e.g., peptidic compounds with methylated amide linkages). As used herein an "analogue" of a compound X refers to a compound that retains chemical structures of X necessary for functional activity of X yet which also contains certain chemical structures that differ from X. An example of an analogue of a naturally occurring peptide is a peptide which includes one or more non-naturally-occurring amino acids.

As used herein, a "mimetic" of a compound X includes compounds in which chemical structures of X necessary for functional activity of X have been replaced with other chemical structures that mimic the conformation of X. Examples of peptidomimetics include peptidic compounds in which the peptide backbone is substituted with one or more benzodiazepine molecules (see e.g., James, G. L. et al. (1993) *Science* 260:1937–1942).

The inventors, without wishing to be limited to the following, have found a mechanism by which the peptides of the invention are effective, e.g., for treating breast cancer. Mitogen-activated protein kinase (MAPK; ERK1/2) is a signal transducing enzyme that, when activated, phosphorylates serine-118 of the nuclear estrogen receptor (ER). ER Phosphorylation enhances the transcriptional activity of nuclear ER when nuclear ER is liganded to estradiol ($E_2$). Thus, full activation of ER is at least a two-step process involving ER phosphorylation as a threshold, and ER interaction with $E_2$.

The inventors have found that at $10^{-8}$M, $E_2$ activates MAPK, e.g., in T47-D human breast cancer cells and serine-phosphorylates ER. Cells were treated with $E_2$ for 60 m and lysed. The nuclear fraction was isolated, separated by gel electrophoresis of the nucleoproteins, and the proteins were transferred to membranes. The resolved nucleoproteins were immunoblotted with anti-phosphoMAPK (activated MAPK, pMAPK) and anti-phosphoER (pER.) The anti-pER is directed to ER's serine-118. The peptides of the invention, at, e.g., $10^6$M, blocks MAPK $E_2$ activation and $E_2$-induced ER phosphorylation. However, there is no enhancement by $E_2$ of either MAPK activation or ER phosphorylation when $E_2$ is added with the peptides of the invention. It has been shown by Lobehofer et al. (*Cell Growth Differ* 11: 99–110 (2000)) that pharmacological inhibition of MAPK prevents E$_2$-induced mitogenesis in human breast cancer cell line (MCF-7). Therefore, the peptides of the invention block ER phosphorylation, a step which is required for full transcriptional activity of ER, and as such, the peptides of the invention are useful anti-cancer, e.g., breast cancer, agents.

The invention includes methods of treating or preventing breast cancer, comprising administering to a subject in need thereof an agent that blocks or inhibits ER phosphorylation, such that breast cancer is treated or prevented. The action of the agent may: block or inhibit the activation of the nuclear estrogen receptor (ER) by estradiol (E$_2$); or block or inhibit ER transcriptional activity; block or inhibit ER phosphorylation, e.g., at serine-118 of ER; by mitogen-activated protein kinase (MAPK).

The agents that may be used include the peptides comprising a hydrophilic analog of an alpha-fetoprotein, having the structure Xaa$_1$-Xaa$_2$-Xaa$_3$-O-Xaa$_4$-N-Xaa$_5$-G-Xaa$_6$ (SEQ ID NO: 12), wherein Xaa$_1$ is selected from the group consisting of E, Q, and N or an acetylated or acylated derivative thereof;

Xaa$_2$ is selected from the group consisting of M and K, or analogs thereof, such as mehtionine sulfone, D-lysine, or acetylated L-lysine;

Xaa$_3$ is a structure providing steric hindrance and hydrophilicity and can be selected from the group consisting of T and S;

Xaa$_4$ is selected from the group consisting of V, I, L, T, a beta-branched amino acid structure, and a hydrophobic amino acid structure;

Xaa$_5$ is selected from the group consisting of P, O and S; and

Xaa$_6$ is an amino acid structure which may be present or absent; when present, it may be used for cyclization and desirably may be selected from the group consisting of G and N, or a substitution variant, peptidomimetic, retro-inverso isomer, or salt thereof.

The agent may also include one of the following: EKTOVNOGN (SEQ ID NO: 1); QMTPVNPG (SEQ ID NO:2); QMTPVNPGE (SEQ ID NO:3); EMTOVNOG (SEQ ID NO:4); EMTOVNOGQ (SEQ ID NO:5); EMTPVNPG (SEQ ID NO:6); EMTPVNPGQ (SEQ ID NO:7); EMTOVNPGQ (SEQ ID NO:8); and EMTPVNOGQ (SEQ ID NO:9.) or substitution variant, peptidomimetic, retro-inverso isomer, or salt thereof. The peptides may be linear or cyclic.

In another aspect the invention included methods of modulating an interaction between MAPK and ER, comprising adding, to a system containing MAPK and ER, an agent that modulates ER phosphorylation by mitogen-activated protein kinase (MAPK), such that an interaction between MAPK and ER is modulated. In a related aspect the invention includes methods of modulating E$_2$ activation of ER, comprising adding, to a system containing MAPK and ER, an agent that modulates ER phosphorylation by MAPK, such that E$_2$ activation of ER is modulated.

Breast cancer modulators may be identified using a method of the invention which comprises introducing into a system containing MAPK and ER with a putative agent that modulates ER phosphorylation by mitogen-activated protein kinase (MAPK); and determining the ability of the putative modulator to modulate ER phosphorylation in the test sample.

The invention also relates to assays for modulators of MAPK activation of ER (and to the modulators and use thereof in, e.g., treating cancer), wherein MAPK and ER are brought into contact with a putative modulator compound under conditions where ER activation, in the absence of modulator, is capable of occurring; and the degree of modulation of MAPK activation of ER caused by said modulator compound is measured.

In another aspect of the invention, cell-proliferating masses, e.g., breast cancer, may be detected noninvasively in a subject by administering to a subject a light-generating fusion protein (or a cell expressing the light-generating fusion protein), where the light-generating fusion protein includes a ligand binding site; and a targeting moiety which is one of the peptides of the invention; allowing for co-localization of light-generating fusion protein or cell and an entity; and imaging the localized light-generating fusion protein, thereby detecting a cell-proliferating disorder in the subject. The light-generating polypeptide moiety may be a bioluminescent or fluorescent polypeptide moiety, e.g., ferredoxin IV, green fluorescent protein, red fluorescent protein, yellow fluorescent protein, blue fluorescent protein, the luciferase family or the aequorin family.

The fusion proteins noted above are also part of the invention. Desirably the light-generating polypeptide moiety is responsive to phosphorylation changes at or near the cancer site. Fusion proteins may include a breast cancer targeting moiety; and a suicide payload.

A fusion protein comprising a targeting moiety which is one of the peptides of the invention, a suicide protein polypeptide moiety, and a light-generating polypeptide moiety which is responsive to phosphorylation changes at or near said breast cancer site, and methods of killing tumor cells using these proteins, are included in the invention.

Method of monitoring the cell-proliferating disorder treatment are part of the invention also, and involve administering to a subject an effective amount of a light-generating fusion protein of the invention, such that the cell-proliferating disorder is treated, and monitoring the ability of the fusion protein to inhibit cell proliferation by measuring the light generated by the fusion protein.

The invention provides therapeutic compounds that are cell proliferation modulators, preferably inhibitors. These modulators contain amino acid structures that are arranged as a hydrophilic analog of an alpha-fetoprotein. The modulator may be a peptide itself, e.g., an octapeptide like that of SEQ ID NO: 5; a peptidomimetic; or may be in the form of a pharmaceutically acceptable scaffold, such as a polycyclic hydrocarbon to which is attached the necessary amino acid structures for biological and/or chemical activity. The modulators of the invention are distinguished in one aspect over previous compounds in that they are orally active, and therefore do not have to be injected into the patient.

The modulators are typically at least eight amino acids in length and based on an octapeptide structure of Xaa$_1$-Xaa$_2$-Xaa$_3$-O-Xaa$_4$-N-Xaa$_5$-G-Xaa$_6$ (SEQ ID NO: 12), or a salt, retro-inverso isomer, or peptidomimetic thereof. "Xaa" is intended to denote an amino acid structure. Xaa$_1$ may be Glu (E) or Gln (O) or Asn (N), or an acetylated or acylated derivative thereof. Xaa$_2$ may be Met (M) or Lys (K), or analogs or derivatives thereof, e.g., methionine sulfone, D-lysine, L-lysine, or an acetylated or acylated lysine derivative. A biologically active peptide with resistance to proteolysis can be obtained by substituting Xaa$_2$ with acetylated L-lysine, D-lysine, D-ornithine, or L-ornithine. Xaa$_3$ is an amino acid structure providing steric hindrance and/or hydrophilicity (e.g., having a value of ⁻0.5 or greater, as described in U.S. Pat. No. 4,554,101.) and can be selected from the group consisting of Thr (T) and Ser (S). Xaa$_4$ may be Val (V), Ile (I), Leu (L), Thr (T), or an analog or derivative thereof, or a beta-branched, or hydrophobic amino acid structure (e.g., having a value of 0.5 or less, as described in U.S. Pat. No. 4,554,101.) $Xaa_5$ may be Pro (P), hydroxyproline (O) or Ser (S), or an analog or derivative thereof. $Xaa_6$ is an amino acid structure that may be present or absent; when present, it may be used for cyclization and desirably may selected from the group consisting of be Gln (O) and Asn (N), or a substitution variant, peptidomimetic, retro-inverso isomer, or salt thereof.

In certain embodiments, $Xaa_1$ is desirably E; $Xaa_3$ is T; $Xaa_4$ is V; $Xaa_5$ is O. In a particularly preferred embodiment, the peptides comprise the sequence EMTOVNOGQ (SEQ ID NO: 5) or EKTOVNOGN (SEQ ID NO: 1). As noted above, the peptides may be linear or cyclic.

As noted above, modulators of the invention may be in the form of a scaffold to which is attached a structure of at least eight amino acid structures, a hydroxyproline amino acid structure, an asparagine amino acid structure, and a glycine amino acid structure, wherein the amino acid structures are arranged as a hydrophilic analog of an alpha-fetoprotein, and therapeutic compound modulates cell proliferation. Use of a scaffold material such as a is polycyclic hydrocarbon allows flexibility for administration as it presents an active compound which is much less resistant to degradation when administered orally. The arrangement of the amino acid structure in the scaffold is desirably EMTOVNOGQ (SEQ ID NO: 5) or EKTOVNOGN (SEQ ID NO: 1) in the cyclic or linear forms.

In another embodiment, the arrangement of amino acid structures on the scaffold may be a glutamic acid (E) or glutamine (Q) amino acid structure in the first position; a methionine (M) or lysine (K) amino acid structure in the second position; a threonine (T) amino acid structure in the third position; a hydroxyproline (O) amino acid structure in the fourth position; a valine (V), isoleucine (I), or beta-branched amino acid structure in the fifth position; an asparagine (N) amino acid structure in the sixth position; a hydroxyproline (O) amino acid structure in the seventh position; and a glycine (G) amino acid structure in the eighth position.

The invention also includes the peptide EMTOVNOGQ (SEQ ID NO: 5) or EKTOVNOGN (SEQ ID NO: 1) in the cyclic or linear forms, or a substitution variant, peptidomimetic, retro-inverso isomer, or salt thereof. In one embodiment, the glutamic acid (E) may be replaced with glutamine (Q). In another embodiment, the amino group on the glutamic acid (E) is acetylated or acylated. In yet another embodiment, the methionine (M) may be replaced with lysine (K) or an analog thereof. The side chain of the hydroxyproline (O) adjacent to the T and V structures may be modified. The valine (V) may be replaced by a beta-branched amino acid structure or hydrophobic amino acid structure, e.g., isoleucine (I); and/or the hydroxyproline (O) adjacent to the N and G structures may be replaced by serine (S).

Analogues of the modulator compounds of the invention are intended to include compounds in which one or more amino acids of the peptidic structure are substituted with a homologous amino acid such that the properties of the original modulator are maintained. Preferably conservative amino acid substitutions are made at one or more amino acid structures. A "conservative amino acid substitution" is one in which the amino acid structure is replaced with an amino acid structure having a similar side chain. Families of amino acid structures having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Non-limiting examples of homologous substitutions that can be made in the peptidic structures of the modulators of the invention include substitution of D-phenylalanine with D-tyrosine, D-pyridylalanine or D-homophenylalanine, substitution of D-leucine with D-valine or other natural or non-natural amino acid having an aliphatic side chain and/or substitution of D-valine with D-leucine or other natural or non-natural amino acid having an aliphatic side chain.

Acceptable amino acid substitutions are those that do not affect the ability of the peptide to alter cell proliferation. Moreover, particular amino acid substitutions may further contribute to the ability of the peptide to alter cell proliferation and/or may confer additional beneficial properties on the peptide (e.g., increased solubility, etc.). A peptide having an identical amino acid sequence to that found within a parent peptide but in which all L-amino acids have been substituted with all D-amino acids is also referred to as an "inverso" compound. For example, if a parent peptide is Thr-Ala-Tyr, the inverso form is D-Thr-D-Ala-D-Tyr.

In addition to the particular peptides disclosed herein, peptide mutants which have additional amino acid structures modified are also contemplated. Such mutants may be more active and/or more stable for in vitro and in vivo formulations. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences that encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine 0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred. It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid structures: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine ((−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

The term mimetic, and in particular, peptidomimetic, is intended to include isosteres. The term "isostere" as used herein is intended to include a chemical structure that can be substituted for a second chemical structure because the steric conformation of the first structure fits a binding site specific for the second structure. The term specifically includes peptide backbone modifications (i.e., amide bond mimetics) well known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[CH$_2$S], ψ[CH$_2$NH], ψ[CSNH$_2$], ψ[NHCO], ψ[COCH$_2$], and ψ[(E) or (Z) CH=CH]. In the nomenclature used above, ψ indicates the absence of an amide bond. The structure that replaces the amide group is specified within the brackets.

Other possible modifications include an N-alkyl (or aryl) substitution (ψ[CONR]), or backbone crosslinking to construct lactams and other cyclic structures. Other derivatives of the modulator compounds of the invention include C-terminal hydroxymethyl derivatives, O-modified derivatives (e.g., C-terminal hydroxymethyl benzyl ether), N-terminally modified derivatives including substituted amides such as alkylamides and hydrazides and compounds in which a C-terminal phenylalanine structure is replaced with a phenethylamide analogue (e.g., Val-Phe-phenethylamide as an analogue of the tripeptide Val-Phe-Phe).

Modulator compounds of the invention can be prepared by standard techniques known in the art. The peptide component of a modulator can be synthesized using standard techniques such as those described in Bodansky, M. *Principles of Peptide Synthesis*, Springer Verlag, Berlin (1993) and Grant, G. A (ed.). *Synthetic Peptides: A User's Guide*, W.H. Freeman and Company, New York (1992). Automated peptide synthesizers are commercially available (e.g., Advanced ChemTech Model 396; Milligen/Biosearch 9600). Additionally, one or more modulating groups can be attached to the peptidic component by standard methods, for example using methods for reaction through an amino group (e.g., the alpha-amino group at the amino-terminus of a peptide), a carboxyl group (e.g., at the carboxy terminus of a peptide), a hydroxyl group (e.g., on a tyrosine, serine or threonine structure) or other suitable reactive group on an amino acid side chain (see e.g., Greene, T. W and Wuts, P. G. M. *Protective Groups in Organic Synthesis*, John Wiley and Sons, Inc., New York (1991).

The invention also includes peptides of eight to twenty amino acids in length which comprise a hydrophilic analog of an alpha-fetoprotein peptide, e.g., SEQ ID NO: 6, EMTPVNPG. The peptide may be linear or cyclic, and may include (D) as well as (L) amino acids. In one embodiment, the peptide includes an amino acid sequence selected from the group consisting of:

SEQ ID NO: 1: EKTOVNOGN
SEQ ID NO: 2: QMTPVNPG
SEQ ID NO: 3: QMTPVNPGE
SEQ ID NO: 4: EMTOVNOG
SEQ ID NO: 5: EMTOVNOGQ
SEQ ID NO: 6: EMTPVNPG
SEQ ID NO: 7: EMTPVNPGQ
SEQ ID NO: 8: EMTOVNPGQ
SEQ ID NO: 9: EMTPVNOGQ
SEQ ID NO: 10: EMTPVNOG, and
SEQ ID NO: 11: EMTOVNPG, or a substitution variant, peptidomimetic, retro-inverso isomer, or salt thereof.

Dimers of these peptides (such as a peptide having SEQ ID NO: 4 in combination with a peptide having SEQ ID NO: 5, or a peptide having SEQ ID NO: 3 in combination with a peptide having SEQ ID NO: 10), or other multimers (three or more peptides), are also contemplated.

The peptides of the invention are useful in a method of reducing estrogen-stimulated growth of cells. This is accomplished by exposing the cells to the peptide, which can occur in vitro and in vivo. Since tamoxifen (and similar substances) have been used previously in the treatment of breast cancer, the invention also provides a method of reducing estrogen-stimulated growth of cells which further comprises exposing the cells to tamoxifen (used in its broadest interpretation to include analogs and derivatives thereof) before, during, or after exposing the cells to the peptide.

A modulator compound of the invention can be further modified to alter the specific properties of the compound while retaining the ability of the compound to alter cell proliferation. For example, in one embodiment, the compound is further modified to alter a pharmacokinetic property of the compound, such as in vivo stability or half-life. In another embodiment, the compound is further modified to label the compound with a detectable substance. In yet another embodiment, the compound is further modified to couple the compound to an additional therapeutic moiety. Schematically, a modulator of the invention comprising an amino acid core domain coupled directly or indirectly to at least one modifying group can be illustrated as MG-ACD, whereas this compound which has been further modified to alter the properties of the modulator can be illustrated as MG-ACD-CM, wherein CM represents an additional chemical modification.

To further chemically modify the compound, such as to alter the pharmacokinetic properties of the compound, reactive groups can be derivatized. For example, when the modifying group is attached to the amino-terminal end of the aggregation core domain, the carboxy-terminal end of the compound can be further modified. Preferred C-terminal modifications include those which reduce the ability of the compound to act as a substrate for carboxypeptidases. Examples of preferred C-terminal modifiers include an amide group (i.e., a peptide amide), an alkyl or aryl amide group (e.g., an ethylamide group or a phenethylamide group) a hydroxy group (i.e., a peptide alcohol) and various non-natural amino acids. Alternatively, when the modifying group is attached to the carboxy-terminal end of the aggregation core domain, the amino-terminal end of the compound can be further modified, for example, to reduce the ability of the compound to act as a substrate for aminopeptidases.

A modulator compound can be further modified to label the compound by reacting the compound with a detectable substance. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{14}C$, $^{123}I$, $^{124}I$, $^{125}I$, $^{131}I$, $^{99m}Tc$, $^{35}S$ or $^{3}H$. In a preferred embodiment, a modulator compound is radioactively labeled with $^{14}C$, either by incorporation of $^{14}C$ into the modifying group or one or more amino acid structures in the modulator compound. Labeled modulator compounds can be used to assess the in vivo pharmacokinetics of the compounds, for example, for diagnostic purposes.

Preferably, for use as an in vivo diagnostic agent, a modulator compound of the invention is labeled with radioactive technetium or iodine. Accordingly, in one embodiment, the invention provides a modulator compound labeled with technetium, preferably $^{99m}Tc$. Methods for labeling peptide compounds with technetium are known in the art (see, e.g., U.S. Pat. Nos. 5,443,815, 5,225,180 and 5,405,597, all by Dean et al.; Stepniak-Biniakiewicz, D., et al. (1992) *J. Med. Chem.* 35:274–279; Fritzberg, A. R., et al. (1988) *Proc. Natl. Acad. Sci. USA* 85:40254029; Baidoo, K. E., et al. (1990) *Cancer Res. Suppl.* 50:799s–803s; and Regan, L. and Smith, C. K. (1995) *Science* 270:980–982). A modifying group can be chosen that provides a site at which a chelation group for $^{99m}Tc$ can be introduced, such as the Aic derivative of cholic acid, which has a free amino group.

In an alternative chemical modification, a compound of the invention is prepared in a "prodrug" form, wherein the compound itself does not modulate cell proliferation, but rather is capable of being transformed, upon metabolism in vivo, into a modulator compound as defined herein. For example, in this type of compound, the modulating group can be present in a prodrug form that is capable of being converted upon metabolism into the form of an active modulating group. Such a prodrug form of a modifying group is referred to herein as a "secondary modifying group." A variety of strategies are known in the art for preparing peptide prodrugs that limit metabolism in order to optimize delivery of the active form of the peptide-based drug (see e.g., Moss, J. (1995) in *Peptide-Based Drug Design: Controlling Transport and Metabolism*, Taylor, M. D. and Amidon, G. L. (eds), Chapter 18.) Additionally, strategies have been specifically tailored to achieving CNS delivery based on "sequential metabolism" (see e.g., Bodor, N., et al. (1992) *Science* 257:1698–1700; Prokai, L., et al. (1994) *J. Am. Chem. Soc.* 116:2643–2644; Bodor, N. and Prokai, L. (1995) in *Peptide-Based Drug Design: Controlling Transport and Metabolism*, Taylor, M. D. and Amidon, G. L. (eds), Chapter 14.

Further provided is a method of treating or preventing cancer in a subject, which comprises administering to the subject an amount of the peptide sufficient to treat or prevent cancer. Such cancers include estrogen-dependent cancers such as breast cancer, as well as, without limitation, uterine, prostate, colon, skin and ovarian cancers. As stated above, this peptide therapy can be combined with administration of tamoxifen to enhance treatment and/or prevention.

The peptides of the invention have been designed as therapeutic agents that are effective against breast cancer. They may also be used against prostate cancer and other cancers which are affected by the steroid hormone/thyroid hormone superfamily of receptors. It is contemplated that these peptides or analogs can serve as first-line defense agents, and alternatively they may serve as adjunct therapeutic agents. For example, the currently utilized drug of choice against breast cancer is tamoxifen, but tamoxifen suffers from a side effect of causing uterine cancer in 0.2% of users. The peptides of the invention inhibit the uterine growth that is stimulated by tamoxifen, and are intended to be useful in adjunct therapy along with tamoxifen.

Other endocrine-related situations in which these peptides might be active include those where AFP has been shown to improve symptoms, such as inflammatory diseases like rheumatoid arthritis. AFP has also been shown to play a therapeutic role in myasthenia gravis and an AFP analog may be useful in this situation. AFP has been reported to play a role in maternal tolerance of the fetus, and therefore an active analog of AFP should have use in organ transplant rejection. Also, use against lymphoproliferative disorders would be appropriate. Since AFP and AFP analogs dampen the response to estrogen and, in all likelihood, progesterone, an AFP analog may be useful in situations such as birth control, abortion, endometriosis, and menopause. For example, post-menopausal estrogen supplementation for bone effects might be a situation in which adjunct treatment with these peptides may prove effective.

These peptides, which are derivatives of a safe, naturally-occurring protein (AFP), are likely to be significantly less toxic than tamoxifen or raloxifene. These analogs may thus be useful as preventive agents so that breast (or prostate or other) cancers do not occur. By modifying these agents with radiolabel or other identifiable means, they can also serve as agents for early detection of breast (or other) cancers.

The inventors, while not wishing to be limited to a particular method or theory of how the present invention operates, have performed experiments using T-47D cells cultured with estradiol plus peptides of the invention, estradiol alone, peptide alone, or no additives (control). It was found that the level of MAP kinase enzyme (nuclear as well as cytoplasmic) that is induced by estradiol alone is reduced by half in cells cultured with estradiol plus peptide. There was a corresponding reduction in the phosphorylation of serine 118 on the estrogen receptor. Treatment with peptide alone produced no effect on the level of MAP kinase.

In a cell-free system, it has been established that peptide does not compete with estrogen for binding to the estrogen receptor. In mice, we have found that daily administration of therapeutic doses of peptide does not reduce the level of serum estrogen. In fact, it appears that administration of therapeutic doses of peptide does lead to a slight increase in levels of both estrogen and progesterone. Thus it appears that the peptides of the invention may be used, particularly in combination with estradiol, in applications where, e.g., competitive competition of the therapeutic agent with the estrogen receptor is undesirable, or where it is undesirable to alter estrogen levels.

The preferred route of administration of peptides is currently injection, which may be acceptable for treatment of cancer or for early detection of cancer. For prevention, transdermal administration of peptides may be preferable, so that administration by means of a patch that may be worn while delivering a prescribed dose of drug should be considered.

Antibodies to the peptides have commercial value for use in measuring the concentration of drug in serum, and for other reasons. Similarly, radiolabeled (or otherwise labeled) peptides and peptidomimetics can be used for detecting such agents in serum or for investigational purposes such as exploring the mechanism of action of these agents.

In the context of this invention, to "expose" cells (including the cells of tissues) to a peptide means to add the peptide, usually in a liquid carrier, to a cell suspension or tissue sample in vitro, or to administer the peptide to cells or tissues within an animal (including a human) subject in vivo.

For therapeutics, the formulation of therapeutic compositions and their subsequent administration is believed to be within the skill in the art. In order to improve stability and shelf life, the peptide may be formulated as a composition including a stabilization excipient such as dodecyl maltoside or mannitol. In general, for therapeutics, a patient suspected of needing such therapy is given a peptide in accordance with the invention, commonly in a pharmaceutically acceptable carrier, in amounts and for periods which will vary depending upon the nature of the particular disease, its severity and the patient's overall condition. The pharmaceutical compositions may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip or infusion, subcutaneous, intraperitoneal or intramuscular injection, pulmonary administration, e.g., by inhalation or insufflation, or intrathecal or intraventricular administration.

The peptide drugs, and peptidomimetics thereof (including mimotopes and anti-mimotopes) can be made using various methods known in the art. A monoclonal antibody can be prepared which specifically binds to the peptide, thereby interfering with activity. The monoclonal antibodies can be produced by hybridomas. A hybridoma is an immortalized cell line which is capable of secreting a specific monoclonal antibody. In general, techniques for preparing polyclonal and monoclonal antibodies as well as hybridomas capable of producing the desired antibody are well known in the art (see Campbell, A. M., *Monoclonal Antibody Technology: Laboratory Techniques in Biochemistry and Molecular Biology*, Elsevier Science Publishers, Amsterdam, The Netherlands (1984); St. Groth, et al., *J Immunol Methods* 35:1–21 (1980)). Any animal (mouse, rabbit, etc.) known to produce antibodies can be immunized with the peptide (or an antigenic fragment thereof). Methods for immunization are well known in the art. Such methods include subcutaneous or intraperitoneal injection of the peptide. One skilled in the art will recognize that the amount of the peptide used for immunization will vary based on the animal which is immunized, the antigenicity of the peptide, and the site of injection.

The peptide that is used as an immunogen may be modified or administered in an adjuvant in order to increase the peptide's antigenicity. Methods of -increasing the antigenicity of a peptide are well known in the art and include, but are not limited to, coupling the antigen with a heterologous protein (such as a globulin or beta-galactosidase) or through the inclusion of an adjuvant during immunization.

For monoclonal antibodies, spleen cells from the immunized animals are removed, fused with myeloma cells, such as SP2/O-Ag myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz, et al., *Exp Cell Res* 175:109–124 (1988)).

Hybridomas secreting the desired antibodies are cloned and the class and subclass are determined using procedures known in the art (Campbell, A. M., *Monoclonal Antibody Technology: Laboratory Techniques in Biochemistry and Molecular Biology*, Elsevier Science Publishers, Amsterdam, The Netherlands (1984)). For polyclonal antibodies, antibody containing antisera is isolated from the immunized animal and is screened for the presence of antibodies with the desired specificity using one of the above-described procedures.

Once a monoclonal antibody that specifically binds to the peptide is identified, the monoclonal can be used to identify peptides capable of mimicking the inhibitory activity of the monoclonal antibody. One such method utilizes the development of epitope libraries and biopanning of bacteriophage libraries. Briefly, attempts to define the binding sites for various monoclonal antibodies have led to the development of epitope libraries. Parmley and Smith developed a bacteriophage expression vector that could display foreign epitopes on its surface (Parmley, S. F. & Smith, G. P., *Gene* 73:305–318 (1988)). This vector could be used to construct large collections of bacteriophage which could include virtually all possible sequences of a short (e.g., six-amino-acid) peptide. They also developed biopanning, which is a method for affinity-purifying phage displaying foreign epitopes using a specific antibody (see Parmley, S. F. & Smith, G. P., *Gene* 73:305–318 (1988); Cwirla, S. E., et al., *Proc Natl Acad Sci USA* 87:6378–6382 (1990); Scott, J. K. & Smith, G. P., *Science* 249:386–390 (1990); Christian, R. B., et al., *J Mol Biol* 227:711–718 (1992); Smith, G. P. & Scott, J. K., *Methods in Enzymology* 217:228–257 (1993)).

After the development of epitope libraries, Smith et al. then suggested that it should be possible to use the bacteriophage expression vector and biopanning technique of Parmley and Smith to identify epitopes from all possible sequences of a given length. This led to the idea of identifying peptide ligands for antibodies by biopanning epitope libraries, which could then be used in vaccine design, epitope mapping, the identification of genes, and many other applications (Parmley, S. F. & Smith, G. P., *Gene* 73:305–318 (1988); Scott, J. K., *Trends in Biochem Sci* 17:241–245 (1992)).

Using epitope libraries and biopanning, researchers searching for epitope sequences found instead peptide sequences which mimicked the epitope, i.e., sequences which did not identify a continuous linear native sequence or necessarily occur at all within a natural protein sequence. These mimicking peptides are called mimotopes. In this manner, mimotopes of various binding sites/proteins have been found.

The sequences of these mimotopes, by definition, do not identify a continuous linear native sequence or necessarily occur in any way in a naturally occurring molecule, i.e. a naturally occurring protein. The sequences of the mimotopes merely form a peptide which functionally mimics a binding site on a naturally-occurring protein.

Many of these mimotopes are short peptides. The availability of short peptides which can be readily synthesized in large amounts and which can mimic naturally occurring sequences (i.e., binding sites) offers great potential application.

Using this technique, mimotopes to a monoclonal antibody that recognizes the peptide of the subject invention can be identified. Once the sequence of the mimotope is determined, the peptide drugs can be chemically synthesized.

The peptides of the invention can contain any naturally-occurring or non-naturally-occurring amino acids, including the D-form of the amino acids, amino acid derivatives and amino acid mimics, so long as the desired function and activity of the peptide is maintained. The choice of including an (L)- or a (D)-amino acid in the peptide depends, in part, on the desired characteristics of the peptide. For example, the incorporation of one or more (D)-amino acids can confer increased stability on a peptide and can allow a peptide to remain active in the body for an extended period of time. The incorporation of one or more (D)-amino acids can also increase or decrease the pharmacological activity of a peptide.

The peptide may also be cyclized, since cyclization may provide the peptide with superior properties over their linear counterparts. Cyclization is discussed further below.

Modifications to the peptide backbone and peptide bonds thereof can be made to the amino acid, derivatives thereof, non-amino acid moiety or the peptide either before or after the amino acid, derivative thereof or non-amino acid moiety is incorporated into the peptide. What is critical is that such modifications mimic the peptide backbone and bonds which make up the same and have substantially the same spatial arrangement and distance as is typical for traditional peptide bonds and backbones. An example of one such modification is the reduction of the carbonyl(s) of the amide peptide backbone to an amine. A number of reagents are available and well known for the reduction of amides to amines such as those disclosed in Wann et al., *JOC* 46:257 (1981) and Raucher et al., *Tetrahedron Lett* 21:14061 (1980). An amino acid mimic is, therefore, an organic molecule that retains the similar amino acid pharmacophore groups as are present in the corresponding amino acid and which exhibits substantially the same spatial arrangement between functional groups. For example, in evaluating a series of analogs for the nonapeptide (EMTOVNOGQ; SEQ ID NO: 5) using an estrogen-dependent uterine growth inhibition assay, the pharmacophore of the peptide was preferably found to include side chains of V and N, and backbone atoms contributed by T, O, V, N, O, and G. However, as previously discussed, conservative substitutions can be made at these positions without losing full activity.

One skilled in the art, using the identified sequences can easily synthesize the peptides for use in the invention. Standard procedures for preparing synthetic peptides are well known in the art. The novel peptides can be synthesized using, e.g., the solid phase peptide synthesis (sPPS) method of Merrifield, *J Am Chem Soc* 85:2149 (1964) or modifications of SPPS; or, the peptides can be synthesized using standard solution methods well known in the art (see, for example, Bodanzsky, *Principles of Peptide Synthesis*, 2d Ed., Springer-Verlag (1993)). Alternatively, simultaneous multiple peptide synthesis (SMPS) techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, *Proc Natl Acad Sci USA* 82:5131 (1985).

In certain embodiments of the modulator compounds of the invention, an amino acid peptidic structure is coupled directly or indirectly to at least one modifying group (abbreviated as MG). The term "modifying group" is intended to include structures that are directly attached to the amino acid peptidic structure (e.g., by covalent coupling), as well as those that are indirectly attached to the peptidic structure (e.g., by a stable non-covalent association or by covalent coupling to additional amino acid structures, or mimetics, analogues or derivatives thereof, which may flank the amino acid peptidic structure). For example, the modifying group can be coupled to the amino-terminus or carboxy-terminus of an amino acid peptidic structure, or to a peptidic or peptidomimetic region flanking the core domain. Alternatively, the modifying group can be coupled to a side chain of at least one amino acid structure of an amino acid peptidic structure, or to a peptidic or peptidomimetic region flanking the core domain, through a hydroxy group of a tyrosyl structure(s), a serine structure(s) or a threonine structure(s) or other suitable reactive group on an amino acid side chain). Modifying groups covalently coupled to the amino acid peptidic structure can be attached by means and using methods well known in the art for linking chemical structures, including, for example, amide, alkylamino, carbamate, urea or ester bonds.

The term "modifying group" is intended to include groups that are not naturally coupled to natural peptides in their native form. Accordingly, the term "modifying group" is not intended to include hydrogen. The modifying group(s) is selected such that the modulator compound alters, and preferably inhibits, cell proliferation when contacted with the peptides.

In a preferred embodiment, the modifying group(s) comprises a cyclic, heterocyclic, polycyclic or branched alkyl group. The term "cyclic group", as used herein, is intended to include cyclic saturated or unsaturated (i.e., aromatic) group having from about 3 to 10, preferably about 4 to 8, and more preferably about 5 to 7, carbon atoms. Exemplary cyclic groups include cyclopropyl, cyclobutyl, cyclopentyl, cyclohexyl, and cyclooctyl. Cyclic groups may be unsubstituted or substituted at one or more ring positions. Thus, a cyclic group may be substituted with, e.g., halogens, alkyls, cycloalkyls, alkenyls, alkynyls, aryls, heterocycles, hydroxyls, aminos, nitros, thiols amines, imines, amides, phosphonates, phosphines, carbonyls, carboxyls, silyls, ethers, thioethers, sulfonyls, sulfonates, selenoethers, ketones, aldehydes, esters, —$CF_3$, —CN, or the like.

The term "heterocyclic group" is intended to include cyclic saturated or unsaturated (i.e., aromatic) group having from about 3 to 10, preferably about 4 to 8, and more preferably about 5 to 7, carbon atoms, wherein the ring structure includes about one to four heteroatoms. Heterocyclic groups include pyrrolidine, oxolane, thiolane, imidazole, oxazole, piperidine, piperazine, morpholine and pyridine. The heterocyclic ring can be substituted at one or more positions with such substituents as, for example, halogens, alkyls, cycloalkyls, alkenyls, alkynyls, aryls, other heterocycles, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —CF$_3$, —CN, or the like. Heterocycles may also be bridged or fused to other cyclic groups as described below.

The term "polycyclic group" as used herein is intended to refer to two or more saturated or unsaturated (i.e., aromatic) cyclic rings in which two or more carbons are common to two adjoining rings, e.g., the rings are "fused rings". Rings that are joined through non-adjacent atoms are termed "bridged" rings. Each of the rings of the polycyclic group can be substituted with such substituents as described above, as for example, halogens, alkyls, cycloalkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —CF$_3$, —CN, or the like.

A preferred polycyclic group is a group containing a cis-decalin structure. An example of a cis-decalin containing structure that can be used as a modifying group is a cholanoyl structure, such as a cholyl group. For example, a modulator compound can be modified at its amino terminus with a cholyl group by reacting the aggregation core domain with cholic acid, a bile acid. Moreover, a modulator compound can be modified at its carboxy terminus with a cholyl group according to methods known in the art (see e.g., Wess, G. et al. (1993) *Tetrahedron Letters*, 34:817–822; Wess, G. et al. (1992) *Tetrahedron Letters* 33:195–198; and Kramer, W. et al. (1992) *J. Biol. Chem.* 267:18598–18604). Cholyl derivatives and analogues can also be used as modifying groups. For example, a preferred cholyl derivative is Aic (3-(O-aminoethyl-iso)-cholyl), which has a free amino group that can be used to further modify the modulator compound (e.g., a chelation group for $^{99m}$Tc can be introduced through the free amino group of Aic). As used herein, the term "cholanoyl structure" is intended to include the cholyl group and derivatives and analogues thereof, in particular those which retain a four-ring cis-decalin configuration. Examples of cholanoyl structures include groups derived from other bile acids, such as deoxycholic acid, lithocholic acid, ursodeoxycholic acid, chenodeoxycholic acid and hyodeoxycholic acid, as well as other related structures such as cholanic acid, bufalin and resibufogenin (although the latter two compounds are not preferred for use as a modifying group). Another example of a cis-decalin containing compound is 5β-cholestan-3α-ol (the cis-decalin isomer of (+)-*dihydrocholesterol*). For further description of bile acid and steroid structure and *nomenclature*, see Nes, W. R. and McKean, M. L. *Biochemistry of Steroids and Other Isopentanoids*, University Park Press, Baltimore, Md., Chapter 2.

In addition to cis-decalin containing groups, other polycyclic groups may be used as modifying groups. For example, modifying groups derived from steroids or β-lactams may be suitable modifying groups. In one embodiment, the modifying group is a "biotinyl structure", which includes biotinyl groups and analogues and derivatives thereof (such as a 2-iminobiotinyl group). In another embodiment, the modifying group can comprise a "fluorescein-containing group", such as a group derived from reacting an peptidic structure with 5-(and 6-)-carboxyfluorescein, succinimidyl ester or fluorescein isothiocyanate. In various other embodiments, the modifying group(s) can comprise an N-acetylneuraminyl group, a trans-4-cotininecarboxyl group, a 2-imino-1-imidazolidineacetyl group, an (S)-(–)-indoline-2-carboxyl group, a (–)-methoxyacetyl group, a 2-norbornaneacetyl group, a .gamma.-oxo-5-acenaphthenebutyryl, a (–)-2-oxo-4-thiazolidinecarboxyl group, a tetrahydro-3-furoyl group, a 2-iminobiotinyl group, a diethylenetriaminepentaacetyl group, a 4-morpholinecarbonyl group, a 2-thiopheneacetyl group or a 2-thiophenesulfonyl group.

In addition to the cyclic, heterocyclic and polycyclic groups discussed above, other types of modifying groups can be used in a modulator of the invention. For example, hydrophobic groups and branched alkyl groups may be suitable modifying groups. Examples include acetyl groups, phenylacetyl groups, phenylacetyl groups, diphenylacetyl groups, triphenylacetyl groups, isobutanoyl groups, 4-methylvaleryl groups, trans-cinnamoyl groups, butanoyl groups and 1-adamantanecarbonyl groups.

Preferred modifying groups include cis-decalin-containing groups, biotin-containing groups, fluorescein-containing groups, a diethylene-triaminepentaacetyl group, a (–)-menthoxyacetyl group, an N-acetylneuraminyl group, a phenylacetyl group, a diphenylacetyl group, a triphenylacetyl group, an isobutanoyl group, a 4-methylvaleryl group, a 3-hydroxyphenylacetyl group, a 2-hydroxyphenylacetyl group, a 3,5-dihydroxy-2-naphthoyl group, a 3,4-dihydroxycinnamoyl group, a (±)-mandelyl group, a (±)-mandelyl-(±)-mandelyl group, a glycolyl group, a benzoylpropanoyl group and a 2,4-dihydroxybenzoyl group.

Therapeutic kits of the present invention are kits including the peptides of the invention. Such kits will generally contain, in suitable container means, a pharmaceutically acceptable formulation of the peptide(s) in a pharmaceutically acceptable formulation, optionally comprising other anti-cancer agents. The kit may have a single container means, or it may have distinct container means for each compound.

When the components of the kit are provided in one or more liquid solutions, the liquid solution is an aqueous solution, with a sterile aqueous solution being particularly preferred. The compositions may also be formulated into a syringeable composition. In which case, the container means may itself be a syringe, pipette, or other such like apparatus, from which the formulation may be applied to an infected area of the body, injected into an animal, or even applied to and mixed with the other components of the kit.

The components of the kit may also be provided as dried powder(s). When reagents or components are provided as a dry powder, the powder can be reconstituted by the addition of a suitable solvent. It is envisioned that the solvent may also be provided in another container means.

The container means will generally include at least one vial, test tube, flask, bottle, syringe or other container means, into which the therapeutic agent is placed, preferably, suitably allocated. Where a second anti-cancer therapeutic is provided, the kit will also generally contain a second vial or other container into which this agent may be placed. The kits may also comprise a second/third container means for containing a sterile, pharmaceutically acceptable buffer or other diluent.

The kits of the present invention will also typically include a means for containing the vials in close confinement for commercial sale, such as, e.g., injection or blow-molded plastic containers into which the desired vials are retained.

Irrespective of the number or type of containers, the kits of the invention may also comprise, or be packaged with, an instrument for assisting with the injection/administration or placement of the ultimate composition within the body of an animal. Such an instrument may be a syringe, pipette, forceps, or any such medically approved delivery vehicle, such as a transcatheter arterial embolization or needle therapy device as disclosed in, e.g., U.S. Pat. No. 4,536,387.

The peptide compositions of the invention may be administered in combination with one or more chemotherapeutic agents such as CMF (cyclophosphamide, methotrexate, fluorouracil), FAC (fluorouracil, adriamycin, cyclophosphamide), tamoxifen, or other antitumor agents. As will be understood by those of ordinary skill in the art, the appropriate doses of the antiestrogen peptides will be generally around those already employed in clinical therapies wherein such peptides are administered alone or in combination with other antitumor or anticancer agents, including approved chemotherapeutic agents known to those of skill in the art. By way of example only, agents such as cisplatin, and other DNA alkylating may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Further useful agents include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of polynucleotide precursors may also be used. Particularly useful are agents that have undergone extensive testing and are readily available. As such, agents such as 5-fluorouracil (5-FU) are preferentially used by neoplastic tissue; making this agent particularly useful for targeting to neoplastic cells. Although quite toxic, 5-FU, is applicable in a wide range of carriers, including topical; however intravenous administration with doses ranging from 3 to 15 mg/kg/day being commonly used.

Exemplary chemotherapeutic agents that are useful in connection with combined therapy are known in the art. The skilled artisan is directed to, e.g., *Remington's Pharmaceutical Sciences*, 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The peptide compositions may be administered in combination with a variety of pharmaceutical excipients, including stabilizing agents, carriers and/or encapsulation formulations as described herein. In particular, the inventor contemplates the use of liposomal delivery systems employing one or more of the instant peptides coupled with internalization sequences such as those from antennapedia, or by other peptide delivery systems as known to those of skill in the art (Saudek, 1997).

Aqueous compositions of the present invention comprise an effective amount of the peptides of the invention, dissolved or dispersed in a pharmaceutically acceptable carrier or aqueous medium. Aqueous compositions of gene therapy vectors expressing any of the foregoing are also contemplated. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intralesional, or even intraperitoneal routes. The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Therapeutic or pharmacological compositions of the present invention will generally comprise an effective amount of the peptides of the invention, dissolved or dispersed in a pharmaceutically acceptable medium. The phrase "pharmaceutically acceptable" refers to molecular entities and compositions that do not produce an allergic, toxic, or otherwise adverse reaction when administered to a human. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art.

Supplementary active ingredients can also be incorporated into the therapeutic compositions of the present invention. For example, the viral binding peptides may also be combined with peptides including cytotoxic T cell- or T helper cell-inducing epitopes to create peptide cocktails for immunization and treatment. Alternatively, compounds with other known or proposed anti-viral activities may also be added if desired.

The preparation of pharmaceutical or pharmacological compositions containing viral binding peptide or peptides, including dextrorotatory peptides, as active ingredients, will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active peptide, peptides or agents to a small area.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, including the peptides alone, or in conjunction with antifungal reagents. Inhalant forms are also envisioned, which again, may contain active peptides or agents alone, or in conjunction with other agents. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed. As used herein, "pharmacologically effective amount" means an amount of composition is used that contains an amount of the peptide or peptides sufficient to significantly lessen, reduce, eliminate, or treat a breast cancer cell in the host animal (mammal).

In this context, the quantity of peptide(s) and volume of composition to be administered depends on the host animal to be treated. Precise amounts of active peptide required for administration depend on the judgment of the practitioner and are peculiar to each individual. However, the peptides are shown to be particularly effective in vitro with one nanogram/ml giving 40% inhibition. Suitable dosage ranges for use in humans are therefore contemplated to be those which result in similar local concentrations of peptides. Doses in the order of about 1 µg/kg/day to about 500 µg/kg/day, preferably about 10 µg/kg/day to about 200 µg/kg/day, and more preferably about 50 µg/kg/day of active ingredient peptide per individual are contemplated.

A minimal volume of a composition required to disperse the peptide or peptides is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 ml of isotonic NaCl solution and either added to 1000 ml of hypodermolysis fluid or injected at the proposed site of infusion, (see for example, *Remington's Pharmaceutical Sciences* 15th Edition, pages 1035–1038 and 1570–1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

A peptide of the present invention can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

In terms of using peptide therapeutics as active ingredients, the technology of U.S. Pat. Nos. 4,608,251; 4,601,903; 4,599,231; 4,599,230; 4,596,792; and 4,578,770 may be used.

The preparation of more, or highly, concentrated solutions for direct injection is also contemplated, where the use of DMSO as solvent is envisioned to result in extremely rapid penetration, delivering high concentrations of the active agents to a small tumor.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

The active peptides or agents may be formulated within a therapeutic mixture to comprise about 0.0001 to 1.0 mg, or about 0.001 to 0.1 mg, or about 0.1 to 1.0 or even about 10 mg per dose or so. Multiple doses can also be administered In addition to the compounds formulated for parenteral administration, such as intravenous or intramuscular injection, other pharmaceutically acceptable forms include, e.g., tablets or other solids for oral administration; liposomal formulations; time-release capsules; and any other form currently used, including cremes.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25–60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabensas preservatives, a dye and flavoring, such as cherry or orange flavor.

It will naturally be understood that suppositories, for example, will not generally be contemplated for use in treating breast cancer. However, in the event that the proteins, peptides or other agents of the invention, or those identified by the screening methods of the present invention, are confirmed as being useful in connection with other forms of cancer, then other routes of administration and pharmaceutical compositions will be more relevant. As such, suppositories may be used in connection with colon cancer, inhalants with lung cancer and so forth.

Materials and Methods

Cell Lines. T47D and MDA-231 human breast cancer cell lines were purchased from the American Type Culture Collection (Manassas, Va.). Growth medium for T47D cells consisted of RPMI 1640 (Life Technologies, Germantown, Md.) supplemented with 10% fetal bovine serum (Life Technologies) and 8 µg/ml bovine insulin (Sigma, St. Louis, Mo.). Growth medium for MDA-MB-231 consisted of Dulbecco's Modified Eagle Medium (Life Technologies) supplemented with L-glutamine (2 mM), non-essential amino acids (1%, Life Technologies) and bovine insulin (1 µg/ml). The MCF-7 cell line was obtained from Dr. Alberto C. Baldi, Institute of Experimental Biology and Medicine, Buenos Aires, Argentina, and was maintained as previously described by Gierthy et al. (1991). This strain of MCF-7 demonstrated 17β-estradiol ($E_2$) sensitivity in regard to induction of tissue plasminogen activator, cell proliferation and in vivo tumor growth and was sensitive to the suppression of these effects by tamoxifen. Continuous exposure of these cells to 1 µM tamoxifen citrate during routine culture conditions (1:10-subculture ratio once a week) resulted after 6 months in a strain that was resistant to the suppressive effects of tamoxifen in vitro.

Peptide Synthesis. Peptides were synthesized using FMOC solid phase peptide synthesis on a Pioneer Peptide Synthesis System (PerSeptive Biosystems, Inc., Framingham, Mass.) (see also Mesfin et al. 2000). Briefly, peptides were assembled on a solid support (FMOC-Polyethylene-Graft Polystyrene Support) from the C-terminus, reacting the deblocked amino (N)-terminus of support-bound amino acid with the activated carboxyl (C)-terminus of the incoming amino acid to form an amide bond. Amino acids used in the synthesis had their N-amino group protected by the 9 fluorenylmethoxycarbonyl (FMOC) group, which was removed by piperidine at the end of each cycle in the synthesis. Side-chain protecting groups of amino acids were Asn(Trt), Gln(Trt), Glu(OtBu), Hyp(tBu), Thr(tBu) which were deprotected by trifluoroacetic acid (TFA) after peptide synthesis. The carboxyl-group of the amino acid was activated with HATU [o-(7-azabenzotriazol-1-yl)-1,1,3,3-tetramethyluronium hexafluorophosphate] obtained from PerSeptive Biosystems Inc. The specific amino acid derivatives, supports, and reagents used in the synthesis were purchased from PerSeptive Biosystems Inc. and Nova Biochem, San Diego, Calif.

After synthesis was completed, the resin was washed three times with 100% propanol and the cleavage reaction was achieved by incubating the resin in 10 ml trifluoroacetic acid/thioanisole/anisole/1,2-ethanedithiol (90:5:2:3) per 0.5 g resin for 5 hours. The cleavage reaction mixture was filtered using a sintered glass funnel to separate the solid resin from the peptide solution. Filtrate volume was reduced to 1 ml by evaporation facilitated with a gentle stream of air and the peptides were precipitated by addition of 15 ml dry-ice chilled ethyl ether. The peptides were allowed to settle for five minutes at −80° C., and the supernatant was aspirated. The peptides were then washed twice in similar manner with 15 ml of ethyl ether. After three further washings with 15 ml of ethyl acetate:diethylether (1.5:1, room temperature), the peptides were dissolved in deionized water, purified by reverse phase HPLC (see details below), lyophilized, and stored at −20° C.

Cyclization of the Peptides. Cyclization of peptides was accomplished using methods described by Kates et al. (17, 18). Briefly, N-alpha FMOC-L-glutamic acid-alpha-allyl ester at the C-terminus of the synthetic peptide was coupled to the resin via the γ-carboxylic acid. Removal of the Nα-FMOC allowed the remaining amino acids to be incorporated sequentially into the growing peptide. A free alpha-carboxyl group was then generated upon removal of the allyl group from the C-terminal Glu (18). This alpha-carboxyl group was then coupled to the free N-terminal structure of the peptide (while on the resin) in order to generate the cyclic peptide, which was then removed from the resin in such a way as to yield the γ-carboxamido derivative (i.e., Q). The cyclic peptide was then purified and characterized as described below.

Purification of Peptides. Purification of peptides was accomplished using a Waters Delta-Pak $C_{18}$ (19 mm×30 cm) reverse phase column with a pore diameter of 300 Å on a Waters 650E liquid chromatography system equipped with a 486 adjustable absorbance detector and a 600E controller. The column was operated with gradient using 0.1% trifluoroacetic acid in water as solvent A and 0.1% trifluoroacetic acid in acetonitrile as solvent B. The gradient was set as follows: 100% solvent A for the first 4 min, followed by increasing acetonitrile from 0–40% solvent B over the next 35 min, then isocratically at 40% B for 11 min, and followed by a linear gradient of 40–30 100% B over 10 min, all with a flow rate of 7 ml/min. Peptide was monitored at 230 nm and fractions containing pure peptide (>95% purity) were pooled together and lyophilized.

Peptide Characterization. Amino acid analyses of all peptides were performed using the Waters AccQ-Tag amino acid analysis system (19; 20). Peptides were analyzed by mass spectrometry using standard α-cyano-4-hydroxysinnipinic acid and sinnipinic acid matrices. Integrity of cyclized peptides was further validated using the Kaiser test (21~ to ensure absence of free terminal amino group.

Immature Mouse Uterine Growth Assay. A bioassay for anti-estrotrophic activity was performed using an immature mouse uterine growth assay (22). Swiss/Webster female mice, 6–8 g in body weight (13–15 days old), were obtained from Taconic Farms (Germantown, N.Y.). Mice were weighed and distributed into treatment groups (typically 5 mice per group) such that each group contained the same range of body weight. In a typical experiment, each group received two sequential intraperitoneal injections spaced one hour apart. Test material or vehicle control for that material was contained in the first injectant. Estradiol ($E_2$) or vehicle control for $E_2$ was contained in the second injectant. Twenty-two hours after the second injection, uteri were dissected, trimmed free of mesenteries, and immediately weighed. The uterine weights were normalized to mouse body weights (mg uterine weight/g of body weight) to compensate for differences in body weight among litters of the same age. Experiments employed a minimum of five mice per group, and the mean normalized uterine weight ±standard error for each group was calculated. Percent growth inhibition in a test group was calculated from the normalized uterine wet weights as described below.

Growth Inhibition(%)=Full $E_2$-Stimulation in Test Group×100% Full $E_2$-Stimulation–No $E_2$-Stimulation Differences between groups were evaluated, employing the non-parametric Wilcoxon Sum of Ranks test (one-sided). In all cases, growth inhibitions that were greater than 25% were significant at $p \leq 0.05$.

Human Breast Cancer Xenograft Assay. A bioassay for anti-breast cancer activity was performed according to Bennett et al. (23;24). Confluent MCF-7 human breast cancer cells were trypsinized into suspension and pelleted by centrifugation at 200×g. The pellet was then solidified into a fibrin clot by exposing it to 10 μl of fibrinogen (50 mg/ml) and 10 μl of thrombin (50 units/ml). The solid mass of MCF-7 cells was then cut into pieces 1.5 mm in diameter. A tumor segment of 1.5 mm in diameter was implanted under the kidney capsule of an immunodeficient ICR-SCID male mouse (Taconic Farms) that weighed about 25 g. Estrogen supplementation was accomplished by s.c. implantation of a silastic tubing capsule containing solid $E_2$ inserted on the day of tumor implantation. Peptide was injected i.p. every twelve hours at a dose of 1 μg per mouse. Tumor growth was monitored during survival laparotomy at 10 day intervals by measurement of the diameters of the short (d) and long axes (D) of each tumor, using a dissecting microscope equipped with an ocular micrometer. Tumor volumes were calculated using the formula $(\pi/6)(d)^2 D$, assuming the tumor shape to be an ellipsoid of revolution around its long axis (D). There were five to seven replicate mice included in each treatment group. Mean tumor volume ±standard error in each group was calculated for display of growth curves. Significance of differences between groups were tested using the one-sided Wilcoxon Sum of Ranks Test.

Assessment of Estrogen Receptor Antagonism. Commercially obtained rabbit uteri (Pel-Freez Biological, Rogers, Ark.) were used as a source of estrogen receptor. Uteri were pulverized in a stainless steel impact mortar under liquid nitrogen and homogenized (20% w/v) in assay buffer (10 mM Tris (pH 7.4), 1.5 mM EDTA, 10% glycerol, 10 mM monothioglycerol, arid 10 mM sodium molybdate) on ice. Centrifugation (50,000×g) for 1 h yielded a supernatant containing cytosol, which was adjusted with assay buffer to 2.5 mg protein/ml. All incubations were carried out in triplicate, each containing 100 μl of cytosol, 20 μl of 10 mM 6,7-[3H]estradiol (50 Ci/mmol; DuPont Pharmaceuticals Company, Wilmington, Del., U.S.A.), and 80 μl of putative antagonist in assay buffer. Total count tubes received 20 μl of [3H]estradiol and 180 μl of assay buffer. After incubation overnight at 4° C., all but the total count tubes received 300 μl of dextran-coated charcoal suspension; tubes were agitated for 15 min and then centrifuged (1,000×g) for 15 min. Supernatants were decanted into counting vials, scintillant was added, and protein-bound tritium was determined by liquid scintillation counting.

EXAMPLE I

Development of a Synthetic Cyclized Peptide Derived from Alpha-Fetoprotein

Figure 1B:
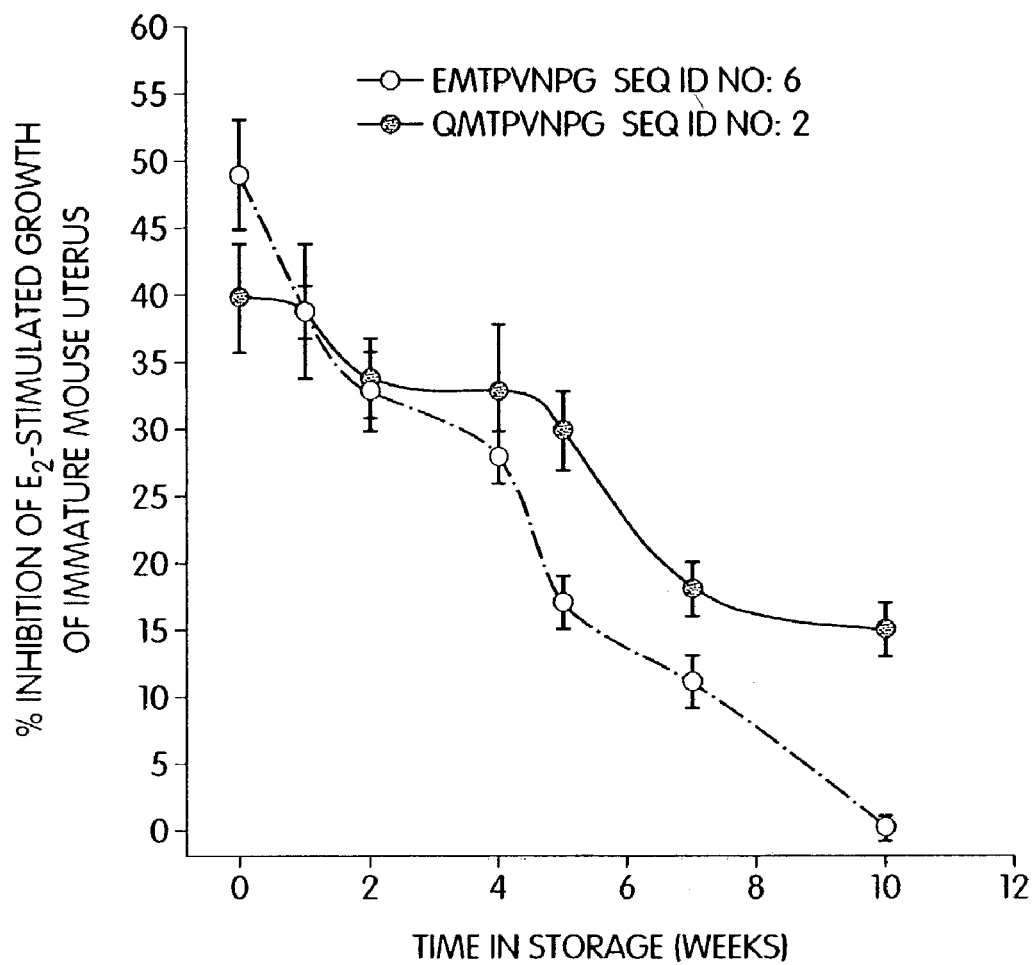

Earlier, it had been shown that an energy-minimized structure of octapeptide SEQ ID NO:6, EMTPVNPG indicated that the peptide had potential to form a horseshoe shaped structure (Mesfin et al. 2000). Energy-minimization studies of an analog of this peptide, that would be generated by substitution of the N-terminal glutamic acid with glutamine (SEQ ID NO:2, QMTPVNPG), indicated that this product would have potential to bow even further inward and form a pseudo-cyclic structure. This pseudo-cyclic structure may have greater structural stability due to hydrogen bonding between the N-terminal glutamine γ-carboxamide group and the C-terminal glycine α-carboxamide. This linear analog (SEQ ID NO:2, QMTPVNPG) was therefore synthesized, and its biological activity was compared to SEQ ID NO:6, EMTPVNPG, in the estrogen-dependent immature mouse uterine growth assay. SEQ ID NO:2, QMTPVNPG inhibited the estrogen-stimulated growth of mouse uterus with an optimal dose of 1 μg/mouse (FIG. 1a), similar to the native octapeptide SEQ ID NO:6, EMTPVNPG. These results suggested that the substitution of glutamic acid to glutamine did not -detract from the biological activity and also did not change the biphasic nature of the dose-response curve. Shelf-life studies indicated that SEQ ID NO:2, QMTPVNPG stored somewhat better than the native octapeptide (SEQ ID NO:6, EMTPVNPG), but its anti-estrotrophic activity also diminished to insignificant levels after five weeks of storage (FIG. 1b), indicating that the putative stabilization was not sufficient to prevent loss of biological activity during storage.

As shown in Table I, aged octapeptide SEQ ID NO:2, QMTPVNPG, stored in the lyophilized state at –20° C. for over one year, was completely biologically inactive. However, brief treatment with 4M urea restored its biological activity, suggesting that this peptide might have aggregated during storage, resulting in loss of biological activity. A scrambled form of the Q octapeptide had no biological activity either with or without urea treatment. The biological activity of stored inactive SEQ ID NO:6, EMTPVNPG was likewise regenerated by 4M urea.

Figure 2A:
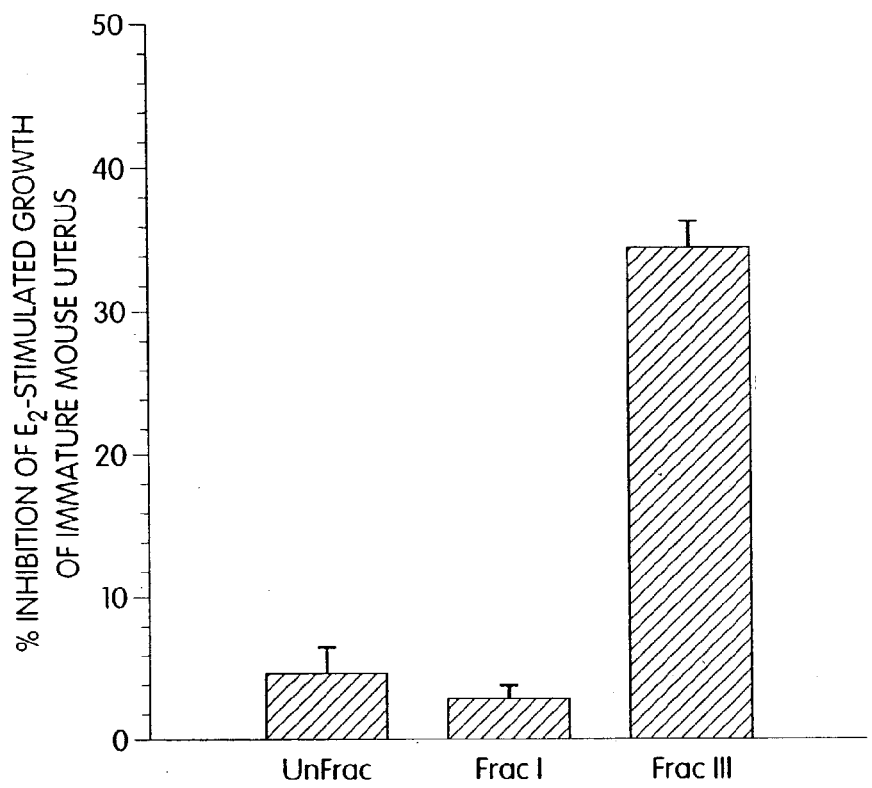
FIGS. 2a and 2b illustrate the anti-uterotrophic activity of fractions from gel-filtration chromatography of stored octapeptide, SEQ ID NO:2, QMTPVNPG. The octapeptide was fractionated using a Waters SW 200 gel-filtration column using phosphate buffered saline pH 7.4 as the mobile phase. Fractions that had significant UV absorbance at 230 nm were collected at twenty second intervals. The first fraction (Frac I), the last fraction (Frac III), and the starting material (UnFrac) were all tested in the immature mouse uterine growth assay as described in FIGS. 1a and 1b. 1 µg of peptide was injected i.p. into mice in all cases, and 20 percent inhibition of $E_2$-stimulated growth was measured.
Figure 2B:
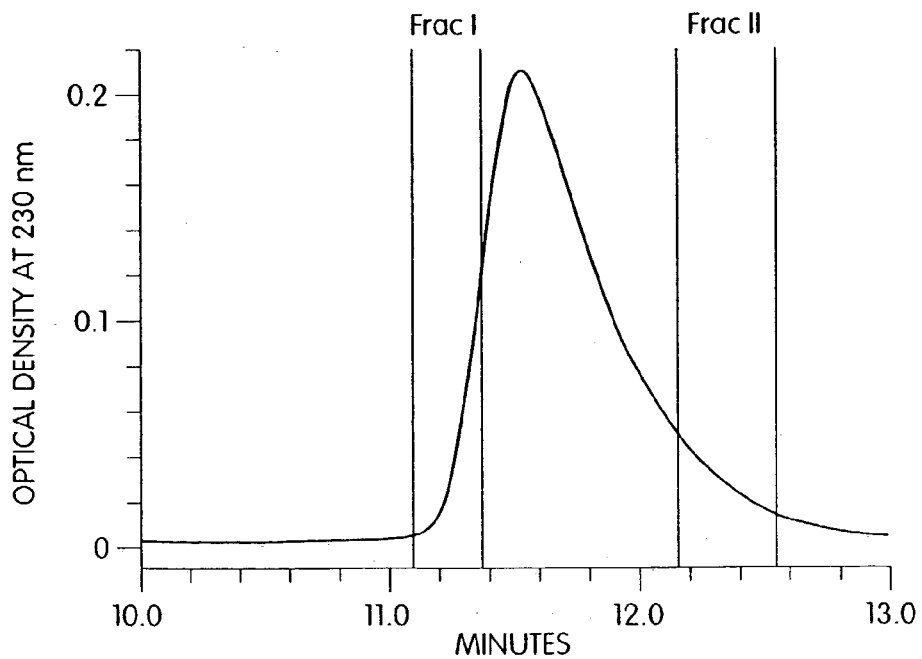
Figure 3A:
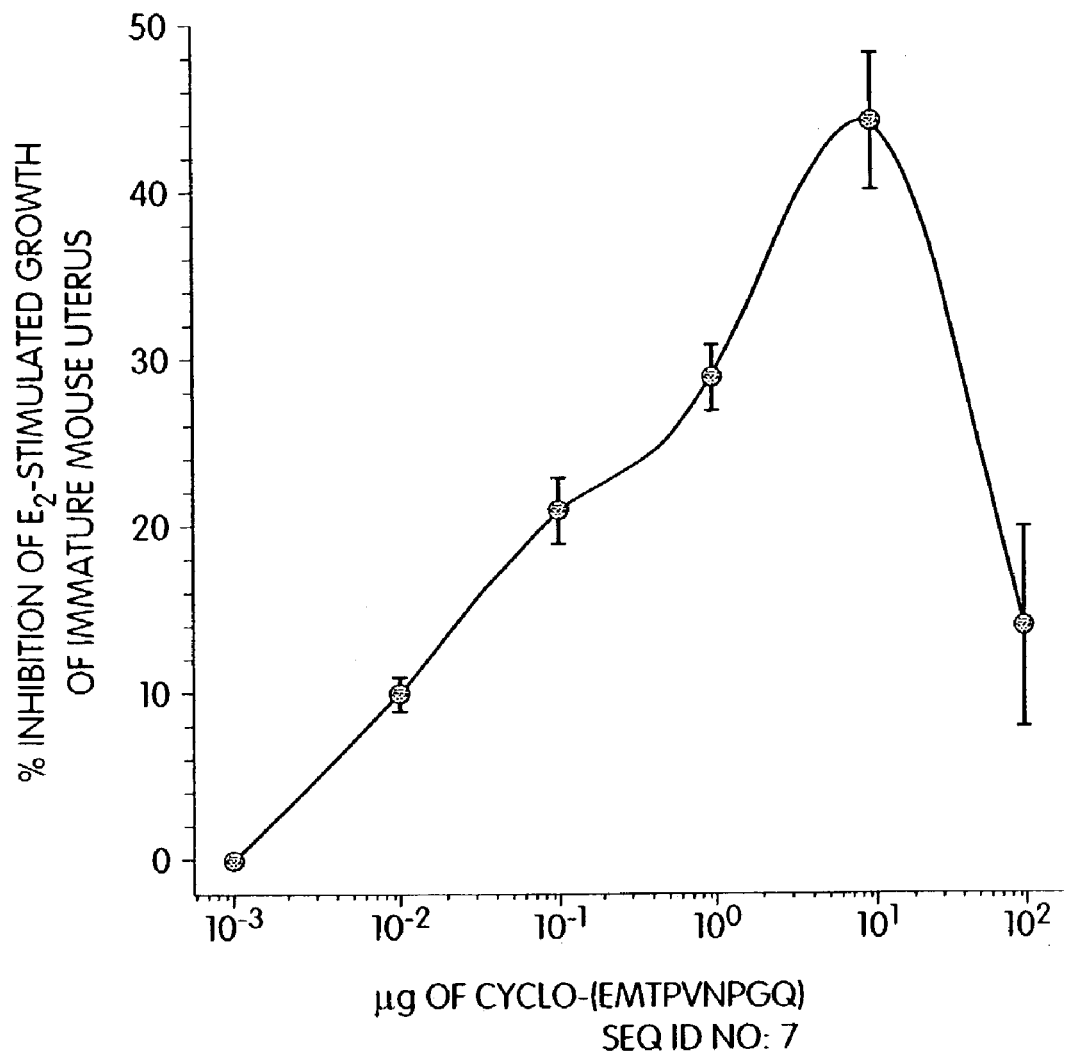
FIGS. 3a and 3b illustrate the anti-uterotrophic activity of cyclo-(SEQ ID NO: 7, EMTPVNPGQ).
Figure 3B:
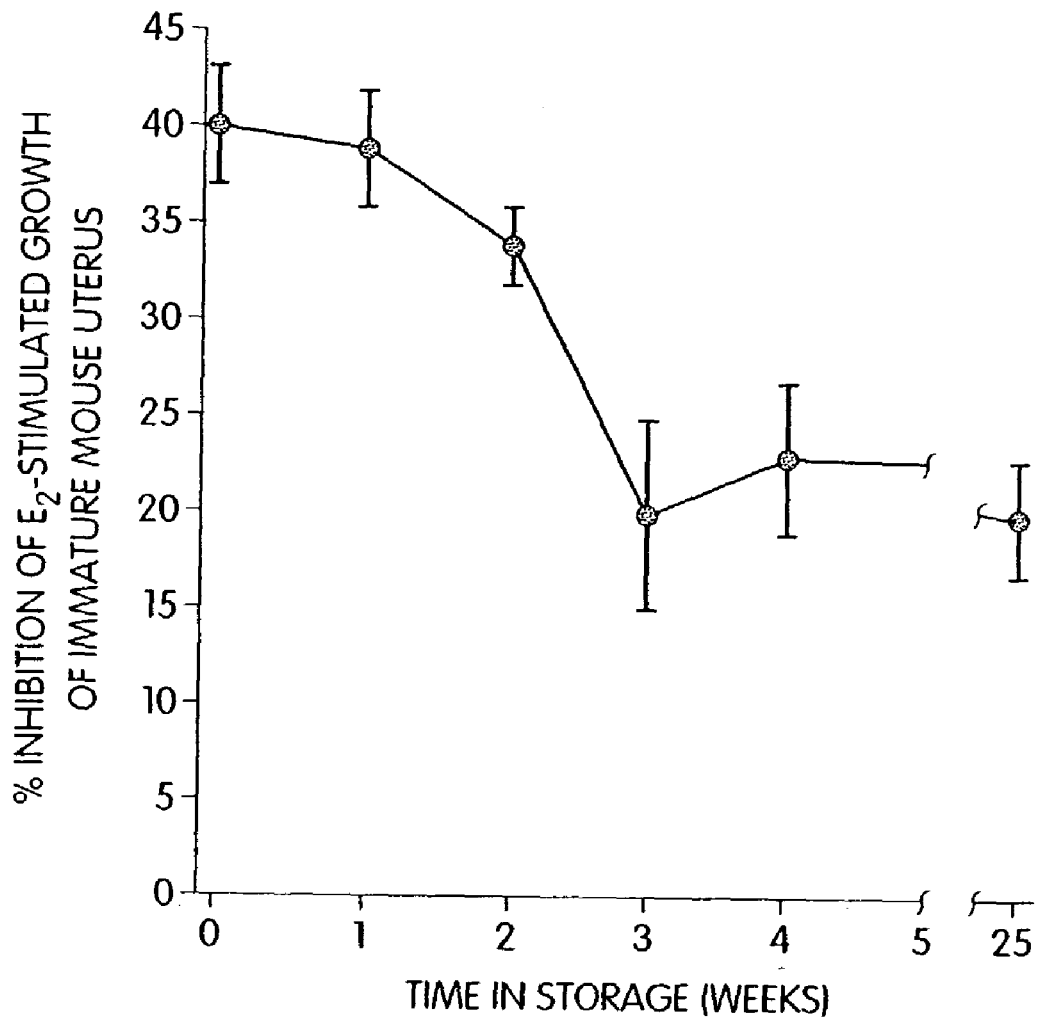
Figure 4B:
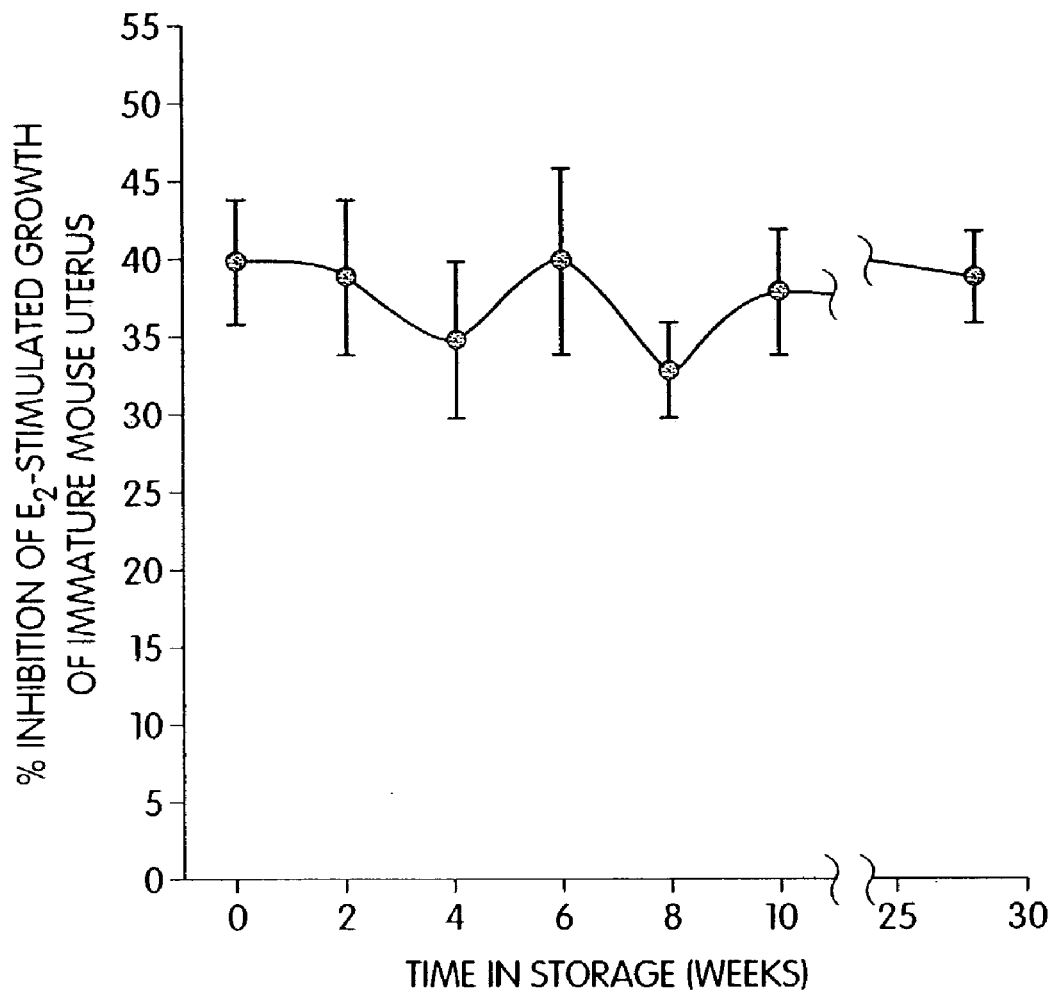
Figure 5:
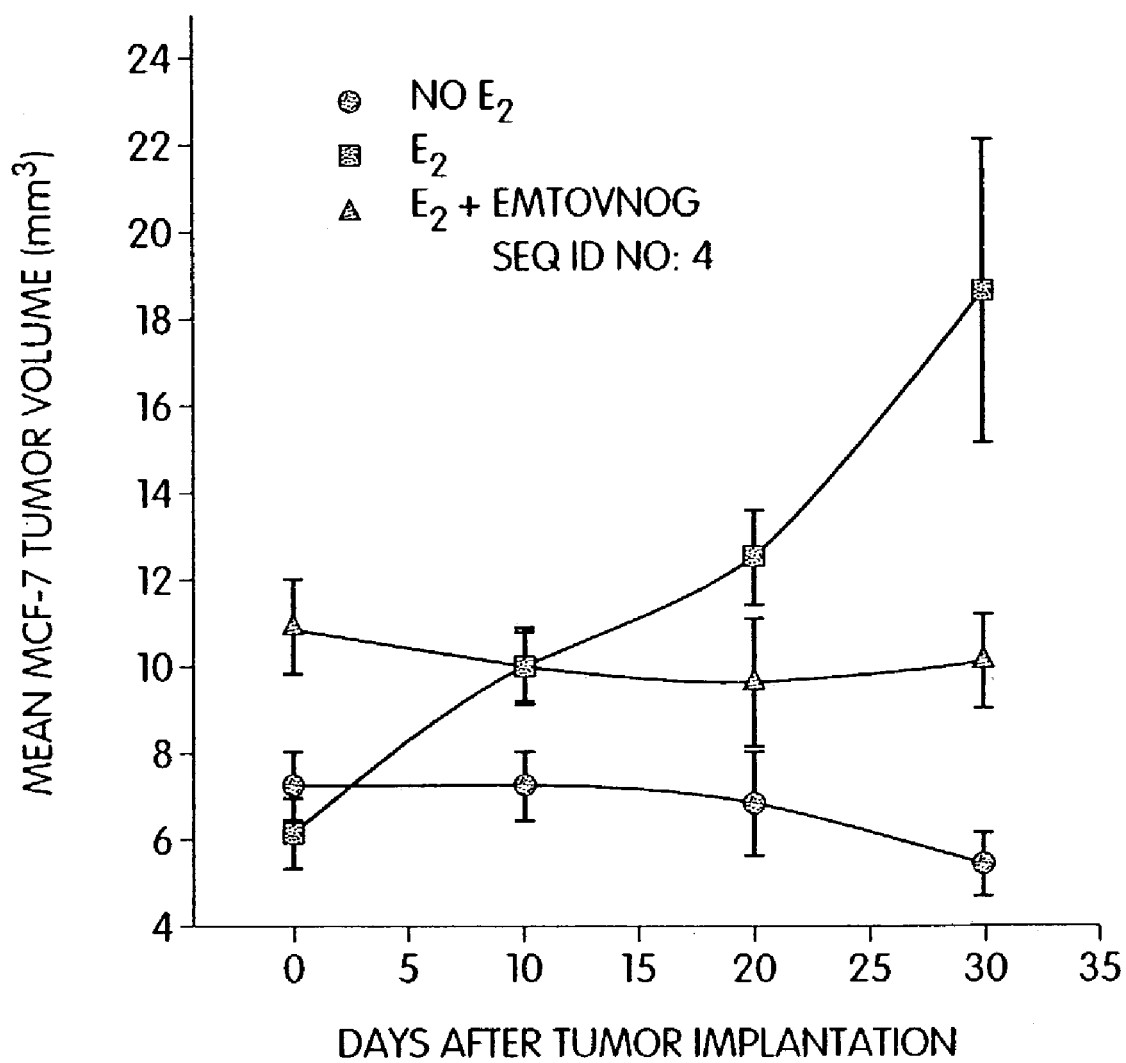
FIG. 5 illustrates the anti-estrotrophic activity of hydroxyproline-substituted linear peptide against MCF-7 human breast cancer xenografts. There were five to eight replicate mice per treatment group. Estrogen was provided via a slow release pellet implanted subcutaneously. Peptide was given twice a day i.p. at a dose of 1 µg per mouse. Tumor volumes in each mouse were measured at the time of tumor implantation and at 10-day intervals thereafter during survival laparotomies. At 30 days after tumor implantation, tumor volumes in the $E_2$+ peptide group were significantly different from tumor volumes in the $E_2$ alone group, $p \leq 0.05$; Wilcoxon ranks-sum test.
Figure 6A:
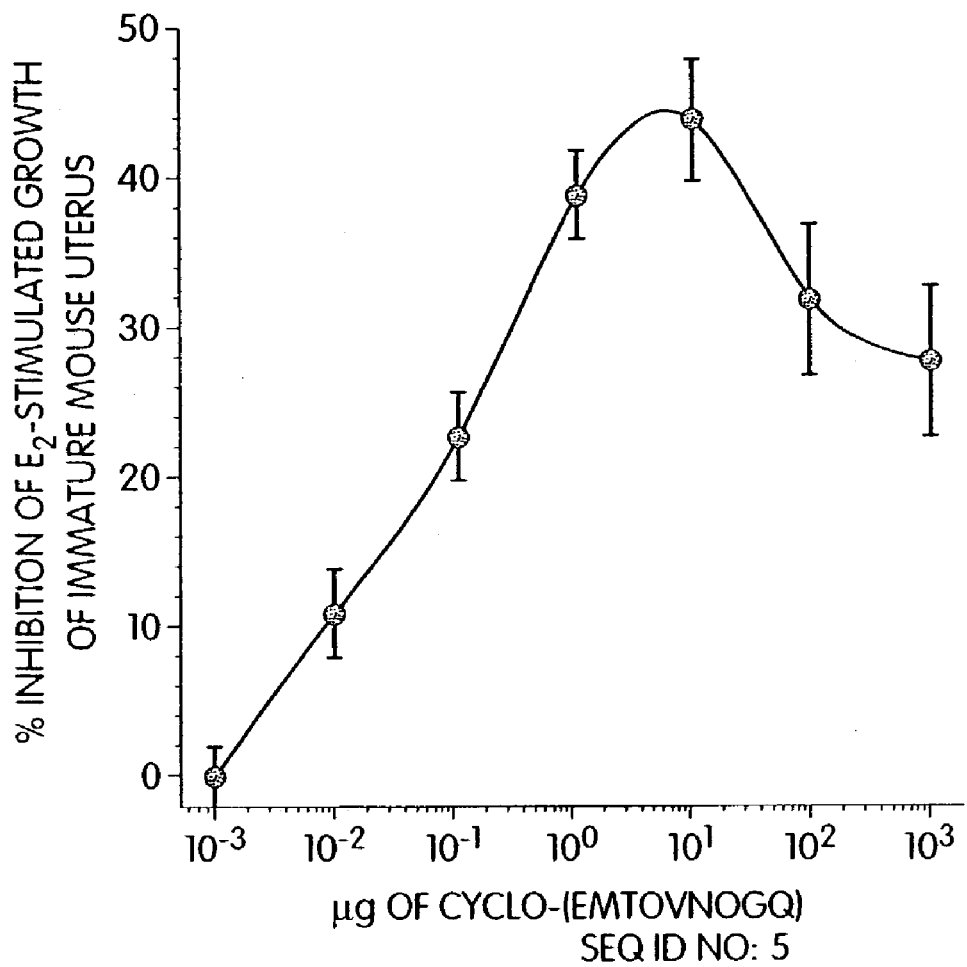
FIGS. 6a and 6b illustrate the anti-uterotrophic activity of cyclized peptide with hydroxyproline substituted for proline.
Figure 6B:
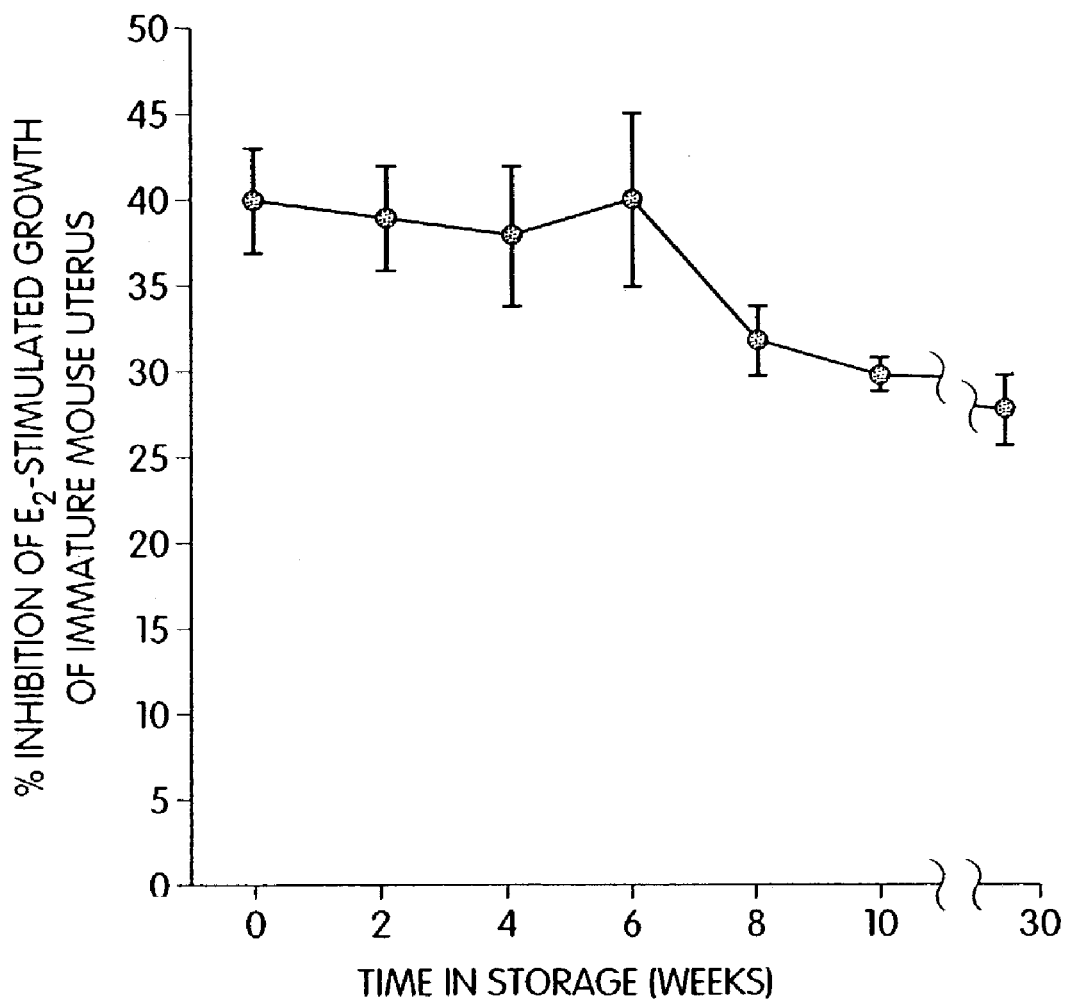
Figure 7:
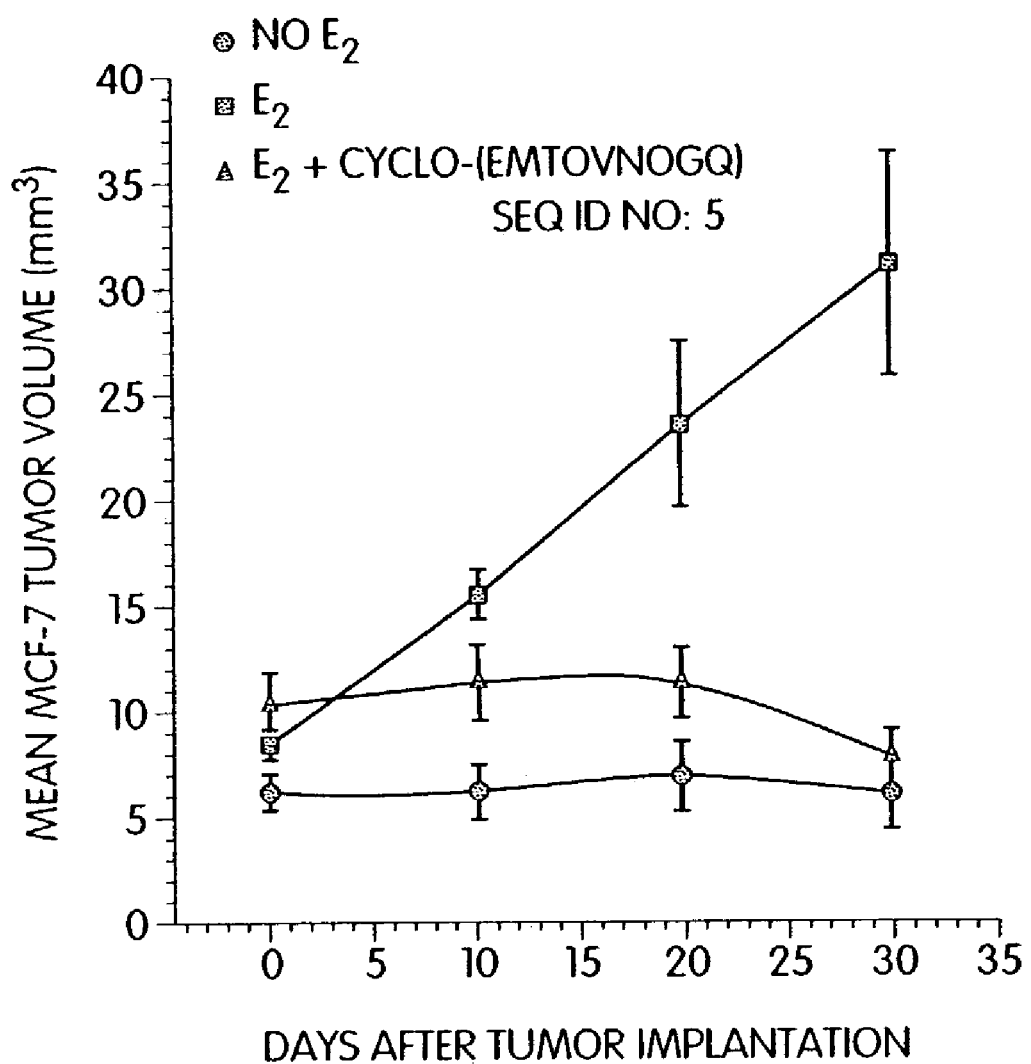
FIG. 7 illustrates the anti-estrotrophic activity of cyclized peptide with hydroxyproline substituted for proline against MCF-7 human breast cancer xenografts. The experimental protocol is described in the legend to FIG. 5, and in the Materials and Methods. At 20 days and 30 days after tumor implantation, tumor volumes in the $E_2$+ peptide group were significantly different from tumor volumes in the $E_2$ alone group, $p < 0.05$; Wilcoxon ranks-sum test.
Figure 8:
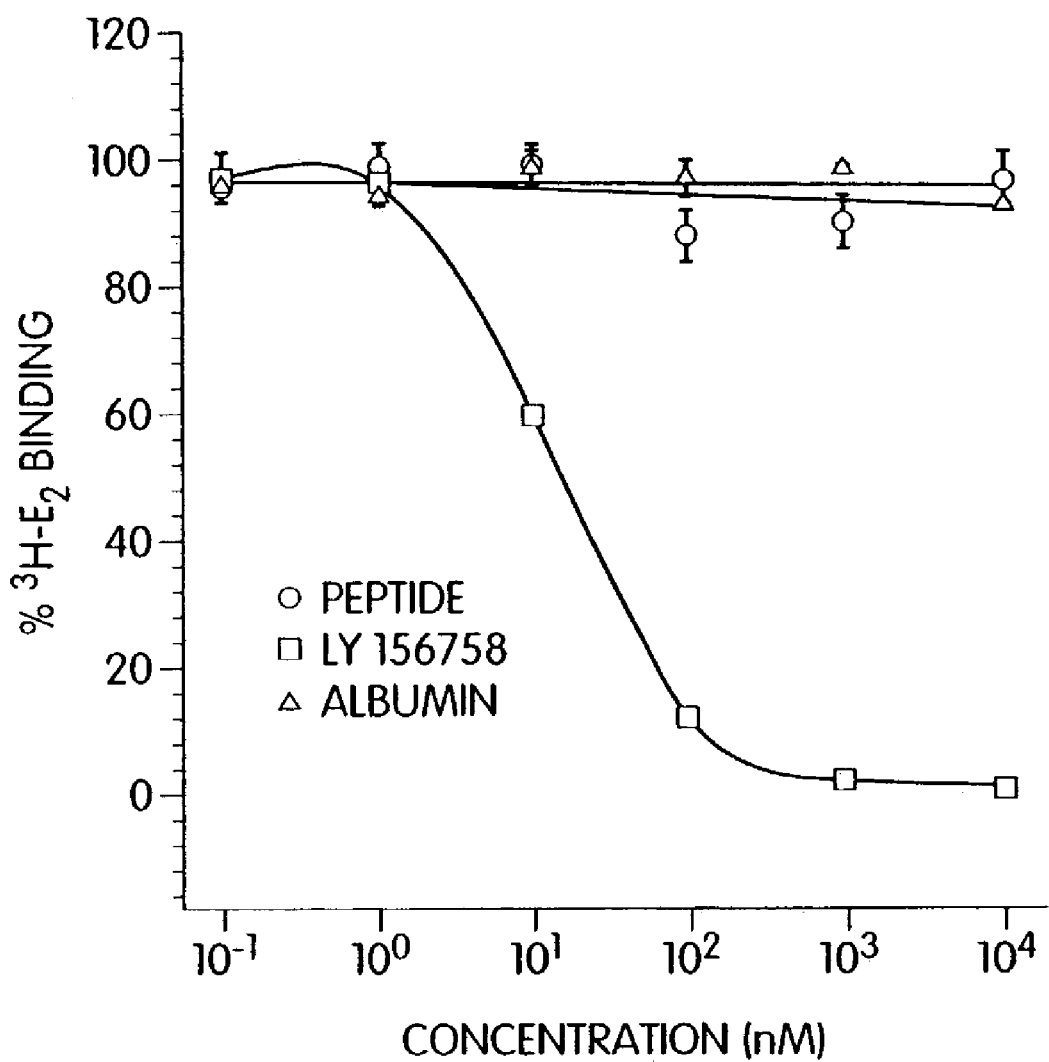
FIG. 8 illustrates the effect of linear hydroxyproline-substituted peptide on binding of $E_2$ to its receptor. Rabbit uterine cytosol was used as a source of estrogen receptor. All incubations were performed in triplicate, each containing 1100 µl of cytosol, 20 µl of 10 nM 6,7-$^3$H estradiol (50 Ci/mmol), and 80 µl of test agent at the final concentrations indicated on the abscissa. Details of the assay are described in Materials and Methods. Concentration of [$^3$E]$E_2$-complex with receptor in the presence of different concentrations of test agent is expressed as a percentage of the amount of complex formed in the absence of test agent.

Gel filtration column chromatography of aged peptide (SEQ ID NO:2, QMTPVNPG) yielded a single peak (FIG. 2b) which became broader as a function of time in storage. This suggested that small aggregates (dimers, trimers) were forming during storage. Although gel filtration chromatography has low resolution for monomers, dimers, and trimers in this size range (841 Da to 2523 Da), the width of the peak suggested that aggregates might be separating from monomer. Fractions from different portions of the broad peak from aged, chromatographed peptide were therefore tested for biological activity. The higher molecular weight fraction (FIG. 2b, left side of peak) was biologically inactive while the lower molecular weight fraction (FIG. 2b, right side of peak) was active in the estrogen-dependent immature mouse uterine growth assay. This suggested that the octapeptide SEQ ID NO:2, QMTPVNPG, like its parent protein and precursor 34-mer peptide (Wu et al. 1985; Eisele et al. 2001), aggregated during prolonged storage in the lyophilized state and only partially dissociated during chromatography, and that the monomeric form of the peptide was the active species. While not especially hydrophobic, the peptide does carry a net charge of only +1 at neutral pH, and taken together with the chromatography and urea evidence, it is reasonable to conclude that hydrophobicity played a role in its aggregation.

In addition to aggregation, small peptides such as octapeptide SEQ ID NO: 6, EMTPVNPG or SEQ ID NO:2, QMTPVNPG have structural flexibility that allows them to attain a variety of different structural conformations. Since it was thought unlikely that all structural conformers of octapeptide SEQ ID NO:6, EMTPVNPG or SEQ ID NO: 2, QMTPVNPG would be biologically active, it seemed appropriate to employ the strategy of conformational constraint in an effort to produce stable analogs. Therefore, cyclic analogs were generated to limit the activity. This greatly expands the active dose range and increases the probability of maintaining an effective dose in humans.

The finding that both linear and cyclized peptides completely stopped the growth of human MCF-7 breast cancer xenografts is highly significant and certainly demonstrates the relevance of these peptides to breast cancer therapeutics. The magnitude of their inhibitory effect was similar to that of tamoxifen which was also shown to stop MCF-7 breast cancer xenograft growth in an earlier study (Bennett et al. 1998). However, their mechanism of action seems to be different from that of tamoxifen, in that they do not interfere with estrogen binding to its receptor. This opens the possibility of combining these agents with tamoxifen or using them in place of tamoxifen when, as so often happens, an estrogen receptor positive breast cancer becomes resistant to tamoxifen (Howell et al. 1995).

EXAMPLE II

Prevention of Growth of Estrogen-Dependent Human Breast Cancers Sensitive and Resistant to Tamoxifen An 8-mer peptide (SEQ ID NO: 4, EMTOVNOG) derived from alpha-fetoprotein (AFP) was compared to tamoxifen for activity against growth of human breast cancer xenografts implanted in immune-deficient mice. Both peptide and tamoxifen prevented growth of estrogen receptor-positive MCF-7 and T47D human breast cancer xenografts. A subline of MCF-7, made resistant to tamoxifen by a six-month exposure to this drug in culture, was found to be resistant to tamoxifen in vivo. Peptide completely prevented the xenograft growth of this tamoxifen-resistant subline of MCF-7. Neither peptide nor tamoxifen were effective in slowing the xenograft growth of the estrogen-receptor-negative MDA-M2-231 human breast cancer. A worrisome toxicity of tamoxifen is its hypertrophic effect on the uterus. In this study, tamoxifen was shown to stimulate the growth of the immature mouse uterus in vivo, and the peptide significantly inhibited tamoxifen's uterotrophic effect. The mechanism of action of peptide is different from that of tamoxifen in that the peptide does not interfere with the binding of [$^3$H]estradiol to the estrogen receptor. In conclusion, AFP-derived peptide appears to be a novel agent that interferes with the growth of tamoxifen-sensitive as well as tamoxifen-resistant estrogen receptor-positive human breast cancers; it inhibits the uterotrophic side effect of tamoxifen; and thus it can be used in combination with or in place of tamoxifen for treatment of estrogen receptor-positive human breast cancers.

Figure 9A:
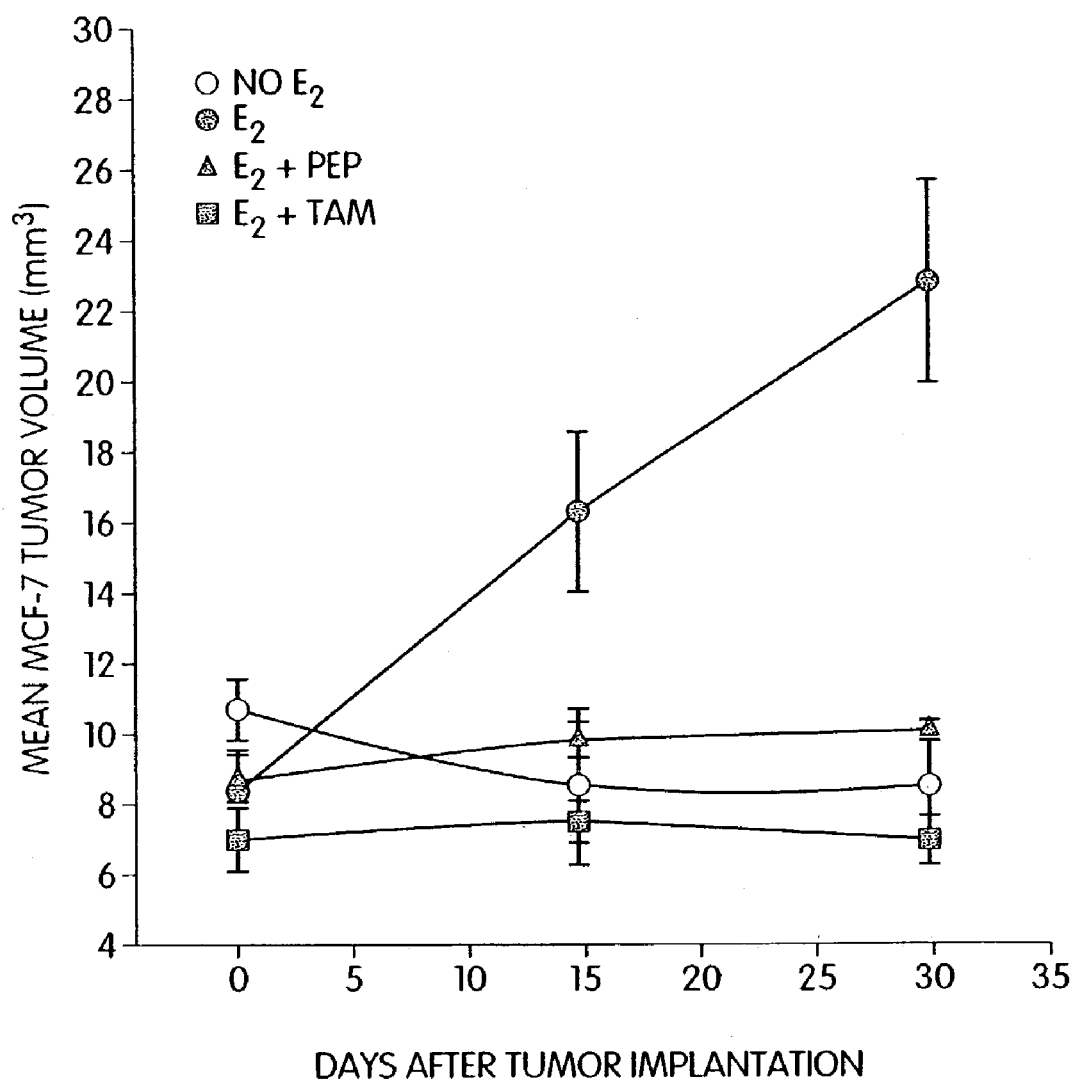
FIGS. 9a and 9b illustrate the effect of AFP-derived peptide on growth of estrogen-receptor-positive MCF-7 and MCF-7/Tam human breast cancer xenografts. Tumors were implanted as described in Materials and Methods. Estrogen (•) was provided via a slow-release pellet of estradiol ($E_2$) implanted s.c. Peptide (▲) was given twice a day i.p. at a dose of 1 g per injection. Tamoxifen (■) was given once a day i.p. at a dose of 50 µg per mouse. Tumor volumes in each mouse were measured at the time of tumor implantation, again at day 15 after tumor implantation during survival laparotomy and again at day 30 after tumor implantation during necropsy. There was a minimum of 5 mice per group.
Figure 9B:
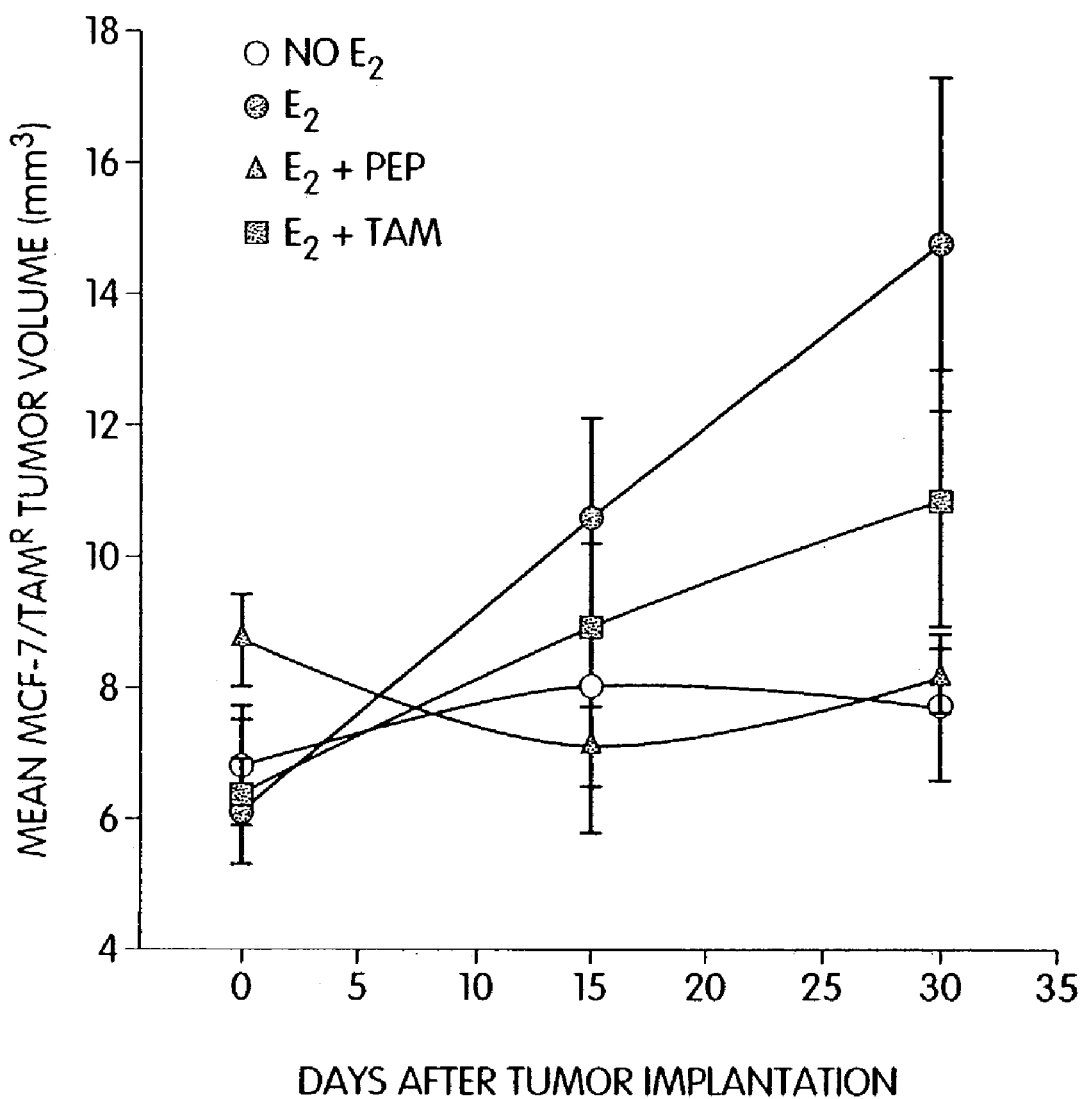
Figure 10:
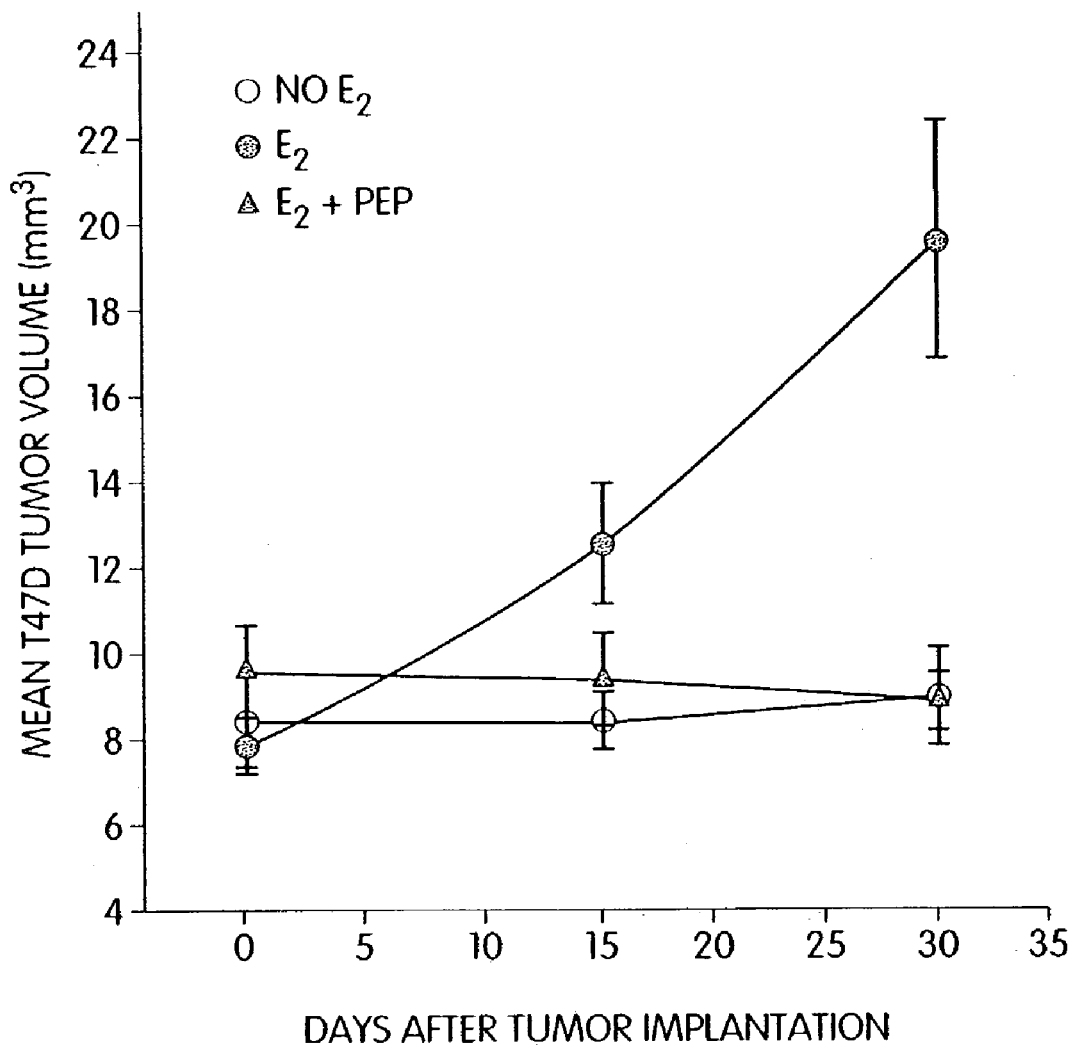
FIG. 10 illustrates the effect of AFP-derived peptide on growth of estrogen-receptor-positive T47D human breast cancer xenografts. See the legend to FIGS. 9a and 9b for the experimental protocol. At day 30 after tumor implantation, tumor volumes in the $E_2$+Pep group were significantly different from tumor volumes in the $E_2$ alone 25 group, p<0.05, Wilcoxon Ranks Sum Test.
Figure 11:
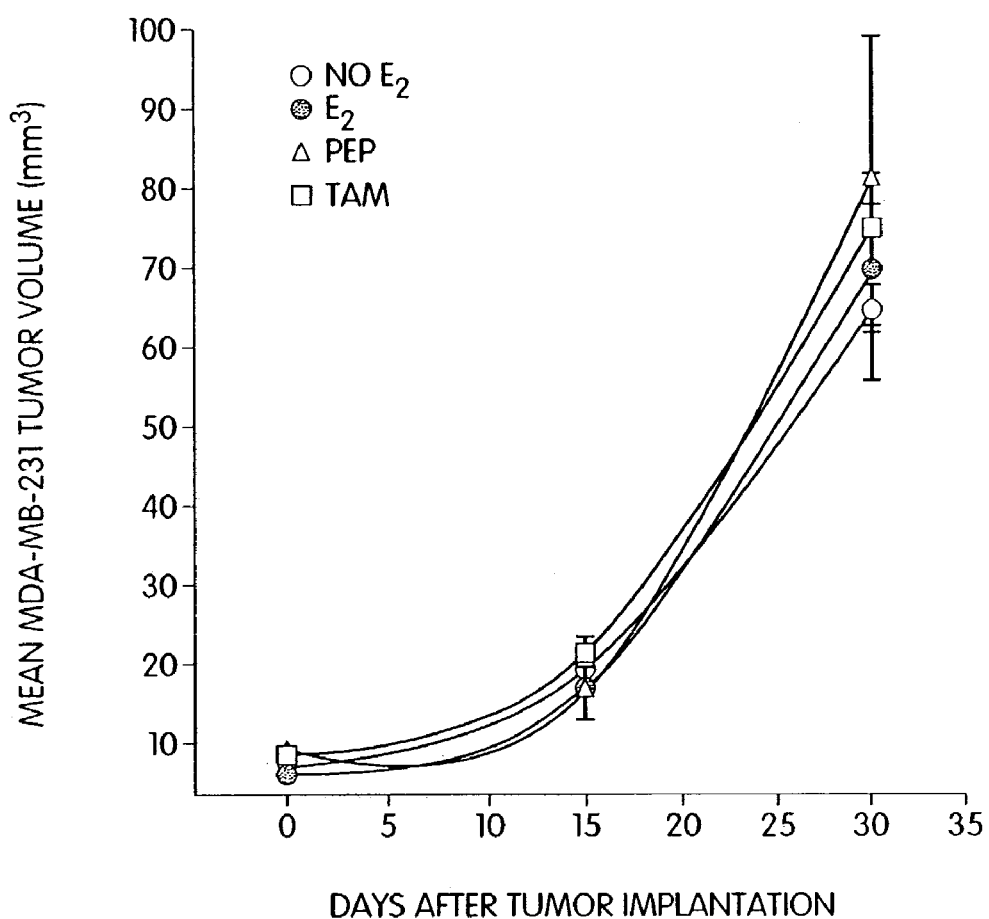
FIG. 11 illustrates the effect of AFP-derived peptide on growth of estrogen-receptor-negative MDA-MB-231 human breast cancer xenografts. See the legend to FIGS. 9a and 9b for the experimental protocol. There were no differences in tumor volumes between any of the groups.

It was determined in a screening assay of the inhibition of $E_2$-stimulated growth of immature mouse uterus by AFP-derived peptide that an effective anti-estrotrophic dose of SEQ ID NO: 4, EMTOVNOG was 0.1 μg to 1.0 μg per mouse. Also, preliminary pharmacokinetic studies suggested that the biological half-life of this peptide in these mice was two to three hours. Therefore, for the breast cancer xenograft studies, it was deemed reasonable to administer this peptide twice a day at a dose of 1.0 μg per i.p. injection into tumor-bearing SCID mice. The ER+ MCF-7 human breast cancer was used as a first step in evaluating the effectiveness of this peptide against human breast cancer. As shown in FIG. 9a, MCF-7 xenografts were completely dependent on estrogen for growth in SCID mice. They underwent an approximate threefold increase in tumor volume in the presence of a slow-release $E_2$ implant during the 30-day observation. Without $E_2$ supplementation, there was no tumor growth. When $E_2$-supplemented mice were given twice-daily injections of 1 μg of peptide, there was no significant increase in tumor volume over the 30-day observation period. Similarly, when $E_2$-supplemented tumors were given once-daily injections of 50 μg of tamoxifen, there was no increase in tumor volume. When a subline of MCF-7 that had been made resistant to tamoxifen in cell culture was used, a rather provocative outcome was obtained. Xenografts of this subline were still completely dependent on B7 for growth (FIG. 9b). With $E_2$ supplementation, they grew somewhat slower than the parent line, approximately doubling in tumor volume over the 30-day observation period. Interestingly, tamoxifen was only minimally effective in retarding the growth of this subline, such that at day 30 after tumor implantation, is the tumor volume in the $E_2$ plus tamoxifen group was not significantly smaller than that found in the group receiving $E_2$ only (FIG. 9b). In contrast, peptide completely stopped the growth of this tamoxifen-resistant NCF-7 subline. The peptide was also tested on ER+ T47D human breast cancer. Like the MCF-7, T47D xenografts were completely dependent on $E_2$ supplementation for growth (FIG. 10) and more than doubled in tumor volume over the 30-day observation period. Daily treatment with peptide during this time interval completely prevented tumor growth (FIG. 10). An ER− human breast cancer, MDA-MB-231, was then tested for sensitivity to peptide. This tumor grew independent of estrogen supplementation and demonstrated a rather aggressive growth rate during the second two weeks of the observation period (FIG. 11). Daily treatment with peptide had no effect on the growth of this tumor at any time during the 30 day observation period (FIG. 11). Similarly, tamoxifen did not affect the growth of this ER− tumor.

Figure 12:
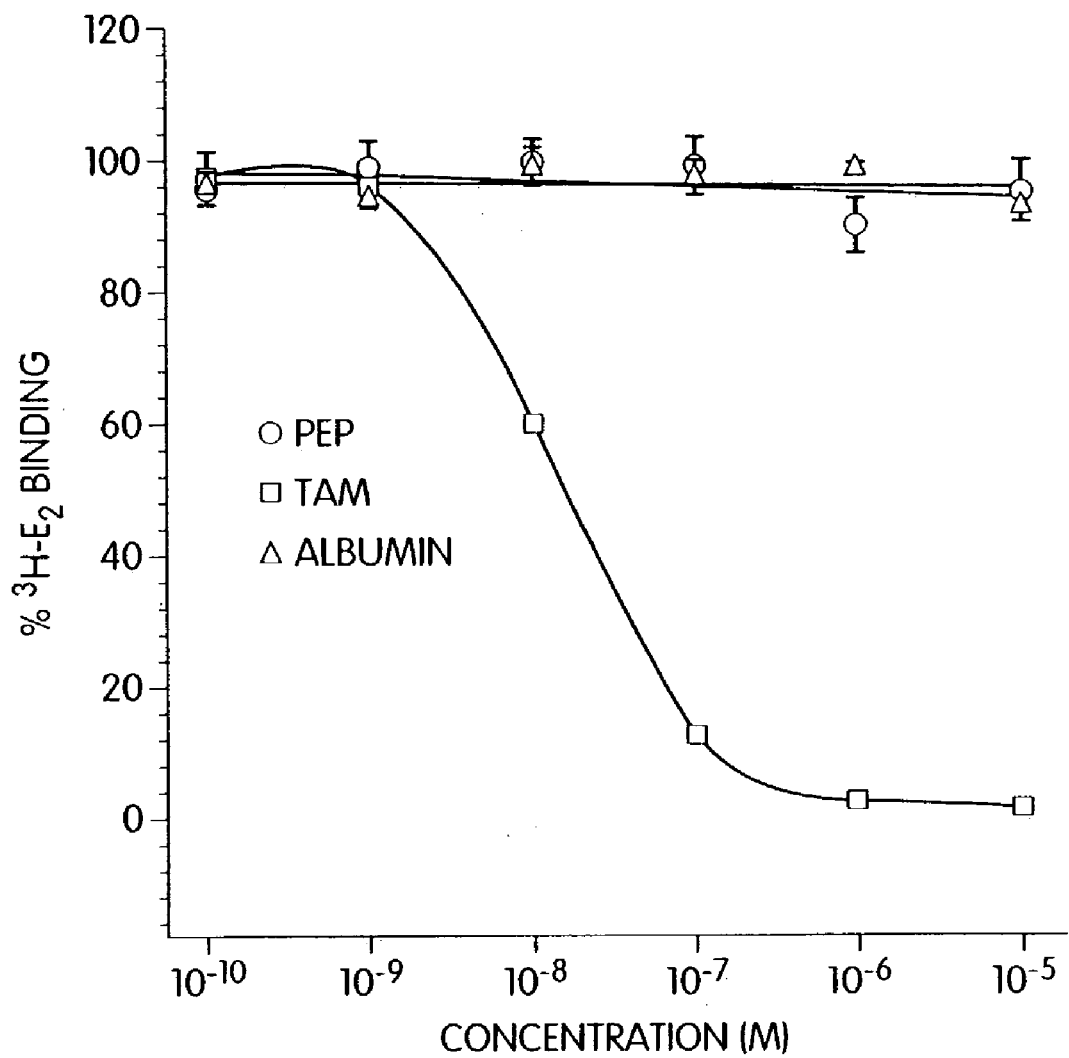
FIG. 12 illustrates the effect of AFP-derived peptide on binding of $E_2$ to its receptor. Rabbit uterine cytosol was used as a source of estrogen receptor. All incubations were performed in triplicate, each containing 100 µl of cytosol, 20 µl of 10 nM 6,7-$^3$H estradiol (50 Ci/mmol), and 80 µl of test agent at the final concentrations indicated on the abscissa. Concentration of [$^3$H]$E_2$-complex with receptor in the presence of different concentrations of test agent is expressed as a percentage of the amount of complex formed in the absence of test agent.

It appears that peptide interferes with E-dependent, but not E-independent, breast cancer growth. As a first step in evaluating the mechanism of action of this peptide, it was compared to tamoxifen as a competitor of $E_2$ for binding to ER. As shown in FIG. 12, tamoxifen exhibits its well-documented interference with $E_2$ binding to ER. The $IC_{50}$ and $IC_{100}$ for tamoxifen were $5\times10^{-8}$M and $5\times10^{-7}$M, respectively. In contrast, peptide produced no interference with $E_2$ binding to ER over a peptide concentration range of $10^{-10}$M to $10^{-5}$M. Thus the mechanism by which peptide interferes with response to estrogen is clearly different from that of tamoxifen.

Figure 13A:
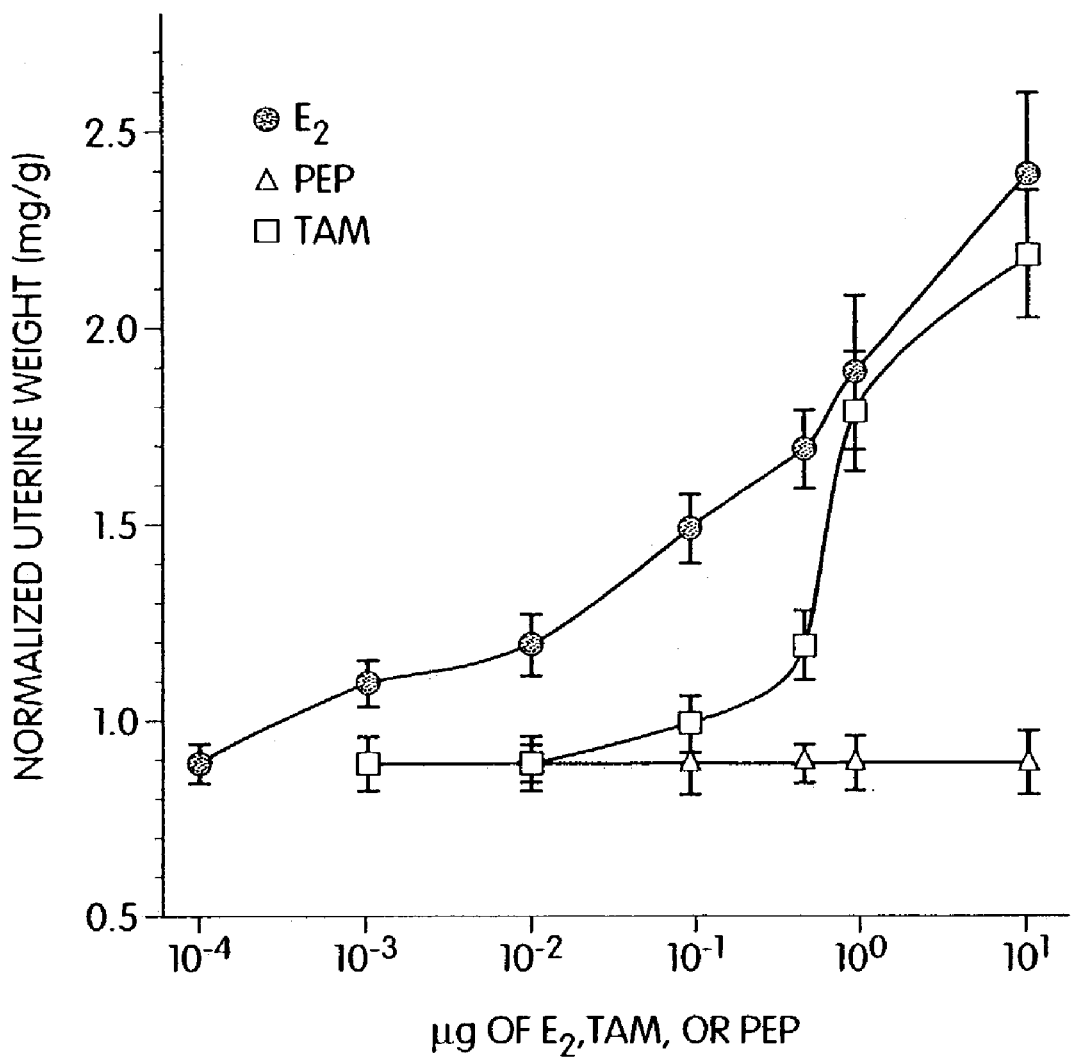
FIG. 13a shows the effect of estradiol ($E_2$), AFP-derived peptide (Pep) and tamoxifen (Tam) on the growth of the immature mouse uterus. The assay procedure is described in the Materials and Methods. Various doses indicated on the abscissa of each test agent were injected i.p. Twenty-two hours later uteri were harvested and weighed. Mean normalized uterine weights (mg uterine weight/g mouse body weight) for each group are shown on the ordinate.
Figure 13B:
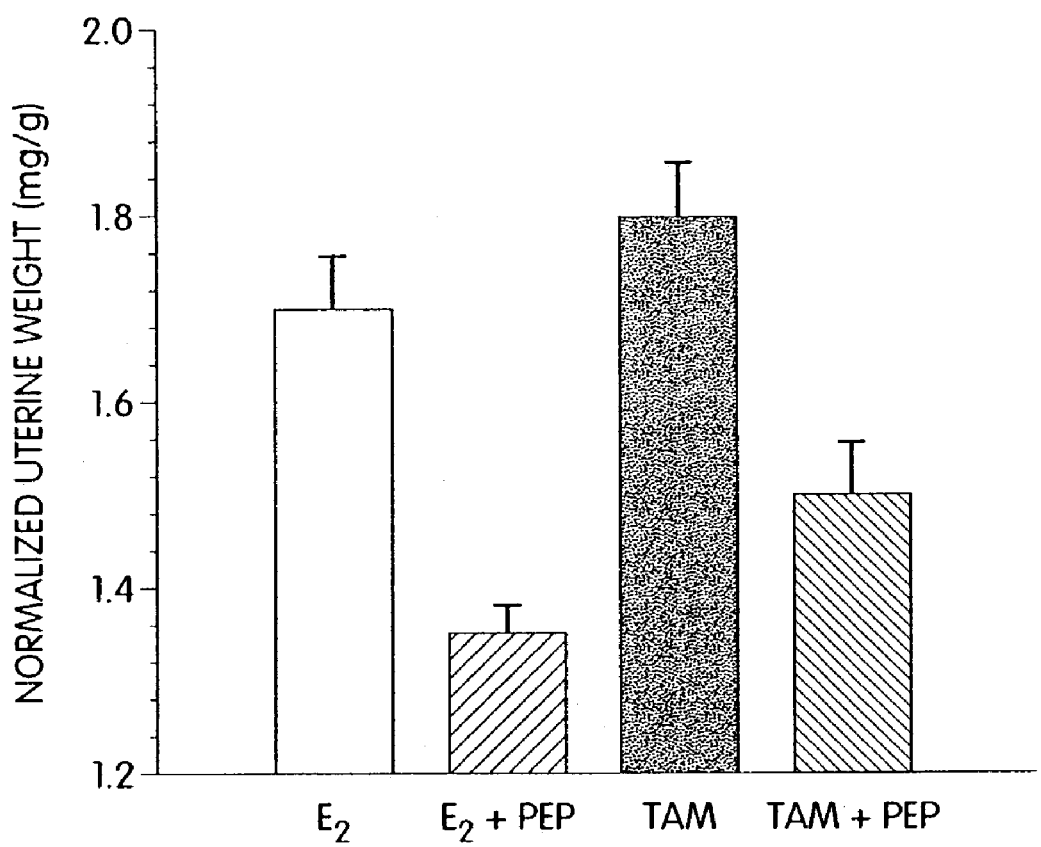
In FIG. 13b, Pep (1 µg) or vehicle (saline, 0.2 ml) were injected i.p. One hour later $E_2$ (0.5 µg) or Tam (1.0 µg) were injected i.p. Twenty-two hours later uteri were harvested and weighed. Normalized uterine weights in the $E_2$+Pep and Tam+Pep groups were significantly different, respectively, from normalized uterine weights in the $E_2$ group and Tam group, p<0.05, Wilcoxon Ranks Sum Test.

A troublesome side effect of tamoxifen in women has been its hypertrophic effect on the uterus (Assikis et al. 1995). It is likewise an estrogen agonist in the murine uterus. As shown in FIG. 13a, tamoxifen stimulated the growth of immature mouse uterus by 50% at a dose of 1 μg/mouse. Tamoxifen's potency was approximately one-tenth that of $E_2$, but nevertheless, FIG. 13a reaffirms that tamoxifen acts as an estrogen agonist on the murine uterus, even though it antagonizes the effect of estrogen on cancer of the breast. Peptide, on the other hand, had no uterotrophic effect whatsoever (FIG. 13a), even at a dose of 10 μg/mouse, which is tenfold greater than the dose employed to prevent breast cancer growth (FIGS. 9a, 9b and 11). Moreover, peptide inhibited the uterotrophic effect of tamoxifen as well as that of estradiol (FIG. 13b).

The results of this study demonstrate that a synthetic 8-mer peptide derived from AFP prevented the $E_2$-stimulated growth of human breast cancer xenografts, including an ER+ breast cancer line that had become resistant to tamoxifen during chronic exposure to this drug in culture. This acquired resistance is similar to what happens in patients whose cancers become resistant to tamoxifen during chronic treatment with this drug (Norris et al. 1999). The peptide had no effect on the growth of ER− breast cancer, which is consistent with the activity found with its parent protein, AFP (Bennett et al. 1998).

TABLE I

Effect of urea on the biological activity of stored peptide

| | Test Agent | Storage Time | % Inhibition of E2-Stimulated Growth of Immature Mouse Uterus ± SE[b] |
|---|---|---|---|
| I | Octapeptide SEQ ID NO: 2 QMTPVNPG | Fresh | 38 ± 3 |
| II | Octapeptide SEQ ID NO: 2: QMTPVNPG | Stored over 1 year | 0 ± 2 |
| III | II after Urea Treatment[a] | None | 34 ± 4 |
| IV | Scrambled Octapeptide | Fresh | 2 ± 5 |
| V | IV after Urea Treatment | None | 0 ± 4 |

[a]Peptide were dissolved in phosphate buffered saline ph 7.4 at a concentration of 200 ug/ml. They were then diluted so 20 μg/ml in 4M urea and incubated at room temperature for one hour. After incubation they were diluted to 2 μg/ml in buffer and 0.5 ml of this preparation (1 μg) was injected into mice as described in legend to FIGS. 1a and 1b.
[b]Assessed as described in legend to FIGS. 1a and 1b.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. An alpha-fetoprotein peptide consisting of the amino acid sequence of EKTOVNOGN (SEQ ID NO:1), wherein said peptide modulates cell proliferation.

2. An alpha-fetoprotein peptide consisting of the amino acid sequence of EKTOVNOGN (SEQ ID NO:1), wherein the lysine residue is D-lysine or acetylated L-lysine.

3. The alpha-fetoprotein peptide of claim 1 or 2, wherein said peptide is cyclic.

4. A fusion protein comprising a breast cancer targeting moiety and a light-generating polypeptide moiety, wherein said breast cancer targeting moiety comprises an alpha-fetoprotein peptide consisting of the amino acid sequence of EKTOVNOGN (SEQ ID NO:1).

5. The fusion protein of claim 4, wherein said light-generating polypeptide moiety is responsive to phosphorylation changes at or near the breast cancer site.

6. A method of treating breast cancer, comprising administering to a subject in need thereof a therapeutically effective amount of the alpha-fetoprotein peptide of claim 1 or 2, wherein said peptide modulates cell proliferation such that breast cancer is treated.

7. The method of claim 6, wherein said alpha-fetoprotein peptide is administered orally.

8. The method of claim 6, further comprising co-administering a therapeutically effective amount of a chemotherapeutic agent.

9. The method of claim 8, wherein said chemotherapeutic agent is tamoxifen.

10. The method of claim 6, wherein said alpha-fetoprotein peptide is cyclic.

* * * * *

UNITED STATES PATENT AND TRADEMARK OFFICE
CERTIFICATE OF CORRECTION

| | | |
|---|---|---|
| PATENT NO. | : 7,122,522 B2 | Page 1 of 1 |
| APPLICATION NO. | : 10/300530 | |
| DATED | : October 17, 2006 | |
| INVENTOR(S) | : Thomas T. Andersen et al. | |

It is certified that error appears in the above-identified patent and that said Letters Patent is hereby corrected as shown below:

Title Page;
Page 1, (73), the Assignee should be: "Albany Medical College" (US)
Albany, NY (US)

Signed and Sealed this
Second Day of August, 2011

David J. Kappos
*Director of the United States Patent and Trademark Office*

UNITED STATES PATENT AND TRADEMARK OFFICE
CERTIFICATE OF CORRECTION

PATENT NO. : 7,122,522 B2
APPLICATION NO. : 10/300530
DATED : October 17, 2006
INVENTOR(S) : Thomas T. Andersen et al.

It is certified that error appears in the above-identified patent and that said Letters Patent is hereby corrected as shown below:

Specification

Column 1, lines 16 to 20, cancel the text beginning with "This invention" and ending with "the invention." and insert the following:

--This invention was made with government support under grant CA87434 awarded by the National Institutes of Health (NIH) and grants DAMD 17-99-1-9054 and DAMD 17-99-1-9370 awarded by the U.S. Army. The government has certain rights in the invention.--

Signed and Sealed this
Fifteenth Day of November, 2016

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 7,122,522 B2 | Page 1 of 1 |
| APPLICATION NO. | : 10/300530 | |
| DATED | : October 17, 2006 | |
| INVENTOR(S) | : Thomas T. Andersen et al. | |

It is certified that error appears in the above-identified patent and that said Letters Patent is hereby corrected as shown below:

In the Specification

Column 1, Line 16, cancel the text beginning with "This invention was made" to and ending "in the invention." in Column 1, Line 20, and insert the following text:
-- This invention was made with government support under CA087434 awarded by the National Institutes of Health, and DAMD17-99-1-9054, and DAMD17-99-1-9370 awarded by the Army Research Laboratory - Army Research Office. The government has certain rights in the invention. --

This certificate supersedes the Certificate of Correction issued November 15, 2016.

Signed and Sealed this
Twenty-seventh Day of August, 2024

Katherine Kelly Vidal
*Director of the United States Patent and Trademark Office*